United States Patent
Simonyan et al.

(10) Patent No.: US 12,128,380 B2
(45) Date of Patent: Oct. 29, 2024

(54) SUPERABSORBENT POLYMER MATERIAL COMPRISING NON-CROSSLINKED POLYACRYLIC ACID POLYMER

(71) Applicant: The Procter & Gamble Company, Cincinnati, OH (US)

(72) Inventors: Arsen Arsenov Simonyan, Koenigstein im Taunus (DE); Natasa Dijakov, Hanau (DE); Dimitris Ioannis Collias, Mason, OH (US); Yiping Sun, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 315 days.

(21) Appl. No.: 17/498,896

(22) Filed: Oct. 12, 2021

(65) Prior Publication Data

US 2022/0143577 A1 May 12, 2022

Related U.S. Application Data

(60) Provisional application No. 63/092,539, filed on Oct. 16, 2020.

(51) Int. Cl.
| | | |
|---|---|---|
| *B01J 20/26* | (2006.01) | |
| *A61F 13/15* | (2006.01) | |
| *A61L 15/60* | (2006.01) | |
| *B01J 20/28* | (2006.01) | |
| *B01J 20/30* | (2006.01) | |
| *C08F 220/06* | (2006.01) | |
| *C08F 222/10* | (2006.01) | |
| *C08J 3/24* | (2006.01) | |

(52) U.S. Cl.
CPC ............ *B01J 20/261* (2013.01); *A61F 13/15* (2013.01); *A61L 15/60* (2013.01); *B01J 20/267* (2013.01); *B01J 20/28007* (2013.01); *B01J 20/3028* (2013.01); *C08F 220/06* (2013.01); *C08F 222/102* (2020.02); *C08J 3/245* (2013.01); *B01J 2220/4812* (2013.01); *B01J 2220/4893* (2013.01); *B01J 2220/68* (2013.01)

(58) Field of Classification Search
CPC ........ B01J 20/26; B01J 20/261; B01J 20/267; B01J 20/28007; B01J 20/3028; B01J 2220/4812; B01J 2220/4893; B01J 2220/68; C08F 222/102; C08F 220/06; A61F 13/15; A61L 15/60; C08J 3/245
USPC .......................................................... 502/402
See application file for complete search history.

(56) References Cited

U.S. PATENT DOCUMENTS

| | | |
|---|---|---|
| 4,910,250 A | 3/1990 | Saotome |
| 7,329,701 B2 | 2/2008 | Herfert et al. |
| 2009/0239966 A1 | 9/2009 | Matsumoto |
| 2012/0298915 A1 | 11/2012 | Okuda |
| 2013/0264517 A1 | 10/2013 | Matsumoto |
| 2014/0193641 A1 | 7/2014 | Torii |
| 2022/0118423 A1 | 4/2022 | Simonyan et al. |

FOREIGN PATENT DOCUMENTS

| | | |
|---|---|---|
| EP | 1621561 A1 | 2/2006 |
| WO | 2004020008 A1 | 3/2004 |

OTHER PUBLICATIONS

All Office Actions; U.S. Appl. No. 17/498,908, filed on Oct. 12, 2021.
PCT Search Report and Written Opinion for PCT/US2021/071817 dated Apr. 2, 2022, 13 pages.
Lim D-W et al: "Synthesis of acrylic acid-based superabsorbent interpenetrated with sodium PVA sulfate using inverse-emulsion polymerization", European Polymer Journal, Pergamon Press Ltd Oxford, GB, vol. 38, No. 3, Mar. 1, 2002 (Mar. 1, 2002), pp. 579-586.

*Primary Examiner* — Edward M Johnson
(74) *Attorney, Agent, or Firm* — Daniel S. Albrecht; Sarah M. DeCristofaro

(57) ABSTRACT

Superabsorbent polymer material comprising cross-linked polyacrylic acid and salts thereof. The superabsorbent polymer material further comprising at least 3.0 weight-%, based on the total weight of the superabsorbent polymer material, of soluble polyacrylic acid polymers. A method for making such superabsorbent polymer materials is also disclosed.

11 Claims, 8 Drawing Sheets

SUPERABSORBENT POLYMER MATERIAL COMPRISING NON-CROSSLINKED POLYACRYLIC ACID POLYMER

FIELD OF THE INVENTION

The present invention is directed to superabsorbent polymer material comprising non-crosslinked polyacrylic acid polymer. The non-crosslinked polyacrylic acid polymer may be obtained from recycled superabsorbent polymer particles which have been (partially) degraded.

BACKGROUND OF THE INVENTION

The use of superabsorbent polymer material (hereinafter referred to as 'SAP material'), typically in particulate form (hereinafter referred to as 'SAP particles'), especially in disposable absorbent articles, is well known in the art. In light of the large quantities of used and disposed absorbent articles, there is a need to find ways to recycle the materials comprised by the absorbent articles. SAP material forms a meaningful portion of the materials comprised by absorbent articles. Hence, recycling of SAP materials from used and disposed absorbent articles is substantial for absorbent article recycling. SAP material derived from used absorbent articles cannot usually be recycled as is but needs to be degraded for recycling. Recently, various methods for SAP material degradation have been developed, including chemical degradation, degradation via UV radiation, ultrasonication, microwave radiation, or mechanochemical degradation.

However, there is a need to recycle and re-use the materials derived from SAP material degradation.

SUMMARY OF THE INVENTION

SAP materials, such as SAP particles used in absorbent articles are most often made of cross-linked polyacrylic acid polymers. Degradation of cross-linked polyacrylic acid polymers into acrylic acid monomers is generally very energy- and/or time-consuming. Depending on the SAP material degradation method, and also on how much time and/or energy is afforded in a SAP material degradation method, the methods do not necessarily lead to complete degradation, i.e. they do not result in acrylic acid monomers. Instead, the methods facilitate degradation into soluble polyacrylic acid polymers. Hence, the cross-links of the insoluble superabsorbent polymer material are broken up, leading to polyacrylic acid polymers (hereinafter also referred to as "s-PAA polymers") which are soluble in aqueous solution.

It is known to use polyacrylic acid oligomers in SAP material making, e.g. in combination with acrylic acid monomers. These oligomers will typically polymerize into the crosslinked acrylic acid network of the SAP material. In contrast thereto, it is believed that polymers of acrylic acid, i.e. molecules with considerably higher molecular weight versus oligomers, do not readily or only to a small extent polymerize into the SAP crosslinked acrylic acid network.

For absorbent articles comprising SAP particles which exhibit good absorbing and containing functions, specific technical requirements need to be fulfilled by the SAP particles, such as sufficient capacity, permeability of the SAP particles. Generally, high capacity and high permeability is desirable. Another important parameter is the amount of extractables of the SAP material. High amounts of extractables are generally not desired for SAP particles, as they negatively impact the performance of the SAP particles. Extractables tend to leach out of the cross-linked polymer network once the superabsorbent polymer material is swollen, thus affecting superabsorbent properties both by loss of superabsorbent mass, and by the osmotic competition of extractables against the insoluble polymer matrix.

It has been found that upon introducing certain s-PAA polymers into SAP particles, the amount of extractables undesirably increases. Upon detailed analysis, the inventors have further found that s-PAA polymers can be comprised by SAP material, such as SAP particles if certain requirements with respect to cross-linked polymer network and configuration of s-PAA polymers are met. In such circumstances, the amount of extractables can be kept low, and parameters reflecting capacity and permeability are not adversely affected compared to SAP material not comprising soluble PAA polymers. This has been proven even for SAP material comprising relatively high amounts of soluble PAA polymers.

In the crosslinked polymer network of the SAP material, neighboring cross-links of the polymer chains comprised by the network are spaced apart by a certain average distance $R_{xl}$. The distance inter alia depends on the amount of cross-linker which has been used upon formation of the SAP material. The distance increases upon swelling of the SAP material, as the polymer chains in the cross-linked network disentangle and expand. The inventors have calculated the average distance $R_{xl}$ between neighboring crosslinks at a SAP material load of 20 g/g (details are given below).

Moreover, to define the spherical characteristic of the s-PAA polymers, the diameter of gyration $2*R_g$ of the s-PAA polymer has been calculated (details are also given below). Radius of gyration (=½ of the diameter of gyration) or gyradius of a body about an axis of rotation is defined as the radial distance to a point which would have a moment of inertia the same as the body's actual distribution of mass, if the total mass of the body were concentrated.

Mathematically the radius of gyration $R_g$ is the root mean square distance of the object's parts from either its center of mass. It is actually the perpendicular distance from point mass to the axis of rotation. One can represent a trajectory of a moving point as a body. Then radius of gyration can be used to characterize the typical distance travelled by this point.

It has been found that if the ratio of diameter of gyration $2*R_g$ to average distance between neighboring cross-links in the polymer network $R_{xl}$ is at least 1.1, the amount of extractables can be effectively reduced. This is due to the fact that the soluble PAA polymers are inhibited from leaking out of the cross-linked network of polyacrylic acid as they are "trapped" in the interstices of the cross-linked network.

The ratio of diameter of gyration $2*R_g$ of the s-PAA polymers comprised by the SAP material to the average distance between neighboring cross-links in the polymer network $R_{xl}$ may be at least 1.2, or at least 1.25, or at least 1.3, or at least 1.4, or at least 1.5. The ratio of $2*R_g$ to $R_{xl}$ may not be more than 5.0, or not more than 4.5, or not more than 4.0, or not more than 3.5, or not more than 3.0, or not more than 2.5.

For the present invention, calculating the ratio of diameter of gyration $2*R_g$ of the s-PAA polymers comprised by the SAP material to the average distance between neighboring cross-links in the polymer network $R_{xl}$, is done with the value for $R_{xl}$ for a SAP material load of 20 g/g, i.e. for SAP material which has absorbed 20 g of saline with 0.9% w NaCl, per gram of dry SAP material.

In addition, the ratio of diameter of gyration $2*R_g$ of the s-PAA polymers comprised by the SAP material to the average distance between neighboring cross-links in the polymer network $R_{xl}$, may also be at least 1,1, or at least 1, 2, or at least 1,25, or at least 1,3, or at least 1.4, or at least 1.5 when the value for $R_{xl}$ is calculated for a SAP material load of 25 g/g, i.e. for SAP material which has absorbed 25 g of saline with 0.9% w NaCl, per gram of dry SAP material.

The average distance between neighboring cross-links in the polymer network $R_{xl}$ may be at least 10 nm, or at least 12 nm, or at least 15 nm, or at least 20 nm, or at least 25 nm. The average distance between neighboring cross-links in the polymer network $R_{xl}$ may be not more than 100 nm, or not more than 70 nm, or not more than 50 nm, or not more than 40 nm, or not more than 35 nm.

The calculation of the average distance between neighboring cross-links in the polymer network $R_{xl}$ for a SAP material load of 20 g/g, i.e. for SAP material which has absorbed 20 g of saline with 0.9% w NaCl, per gram of dry SAP material.

If the ratio of diameter of gyration $2*R_g$ of the s-PAA polymers comprised by the SAP material to the average distance between neighboring cross-links in the polymer network $R_{xl}$, at a SAP material load of 25 g/g is regarded (in addition to the ratio at 20 g/g), then the average distance between neighboring cross-links in the polymer network $R_{xl}$ for a SAP material load of 25 g/g is calculated (in addition to the calculation at 20 g/g), i.e. for SAP material which has absorbed 25 g of saline with 0.9% w NaCl, per gram of dry SAP material.

The diameter of gyration $2*R_g$ of the s-PAA polymers may be at least 15 nm, or at least 20 nm, or at least 25 nm, or at least 30 nm, or at least 35 nm, or at least 40 nm. The diameter of gyration $2*R_g$ of the s-PAA polymers may be not more than 200 nm, or not more than 150 nm, or not more than 100 nm, or not more than 80 nm, or not more than 70 nm.

The present invention relates to superabsorbent polymer material comprising cross-linked polyacrylic acid and salts thereof. The superabsorbent polymer material further comprises at least 3.0 weight-%, based on the total weight of the superabsorbent polymer material, of soluble polyacrylic acid polymers. The cross-linked polyacrylic acid and salts thereof have an average distance $R_{xl}$ between neighboring crosslinks. The at least 3 weight-% of soluble polyacrylic acid polymers have an average diameter of gyration $2*R_g$. The ratio of $2*R_g$ to $R_{xl}$ is at least 1.1.

The soluble polyacrylic acid polymers may have a weight average molecular weight $M_w$ of from 250 kDa to 3 MDa.

The average distance between neighboring cross-links in the polymer network $R_{xl}$ may be at least 10 nm, or at least 12 nm, or at least 15 nm, or at least 20 nm, or at least 25 nm. The average distance between neighboring cross-links in the polymer network $R_{xl}$ may be not more than 100 nm, or not more than 70 nm, or not more than 50 nm, or not more than 40 nm, or not more than 35 nm.

The calculation of the average distance between neighboring cross-links in the polymer network $R_{xl}$ for a SAP material load of 20 g/g, i.e. for SAP material which has absorbed 20 g of saline with 0.9% w NaCl, per gram of dry SAP material.

If the ratio of diameter of gyration $2*R_g$ of the s-PAA polymers comprised by the SAP material to the average distance between neighboring cross-links in the polymer network $R_{xl}$, at a SAP material load of 25 g/g is regarded (in addition to the ratio at 20 g/g), then the average distance between neighboring cross-links in the polymer network $R_{xl}$ for a SAP material load of 25 g/g is calculated (in addition to the calculation at 20 g/g), i.e. for SAP material which has absorbed 25 g of saline with 0.9% w NaCl, per gram of dry SAP material. The diameter of gyration $2*R_g$ of the soluble polyacrylic polymers may be at least 20 nm, and not more than 100 nm, preferably not more than 80 nm.

The superabsorbent polymer material may have a ratio of extractables [weight-%] to capacity (in g/g, measured as CRC according to the test method set out herein) of less than 0.30, or less than 0.28, or less than 0.26.

The superabsorbent polymer material may be at least partially neutralized, preferably from 50% to 95% neutralized.

The superabsorbent polymer material may have an EFFC of at least 25 g/g.

The invention also relates to a method of making superabsorbent polymer material described herein. The method comprises the steps of The SAP material described above can be made by a method wherein SAP material is obtained by polymerizing an aqueous solution comprising the steps of:
a) providing an aqueous solution of polymerizable acrylic acid monomers and/or polymerizable acrylic acid oligomers, optionally neutralizing at least some of the polymerizable acrylic acid monomers and/or polymerizable acrylic acid oligomers;
b) optionally providing one or more ethylenically unsatured co-monomers, optionally neutralizing at least some of the ethylenically unsatured co-monomer of step b);
c) providing one or more crosslinker(s);
d) providing one or more initiator(s);
e) providing at least 3 weight-% of soluble polyacrylic acid polymers based on the total weight of the soluble polyacrylic acid polymers provided in step e) and the monomers, oligomers, co-monomers, crosslinkers and initiators provided in steps a) to d)
f) mixing the aqueous solution of monomers, oligomers, co-monomers, crosslinkers and initiators and soluble polyacrylic acid polymers provided in steps a) to e); and
g) polymerizing the mixture obtained in step f) to obtain a superabsorbent polymer material.

The monomers and/or oligomers provided in method step a) may be neutralized at a degree of neutralization from 40 to 95 mol %.

The optional co-monomers may be provided at less than 25 weight-%, or less than 15 weight-% or less than 10 weight-%, or less than 5 weight-%, or even less than 2 weight-% based on the total weight of the polymerizable acrylic acid monomers and/or polymerizable acrylic acid oligomers.

DETAILED DESCRIPTION OF THE INVENTION

Definitions

Figure 1:
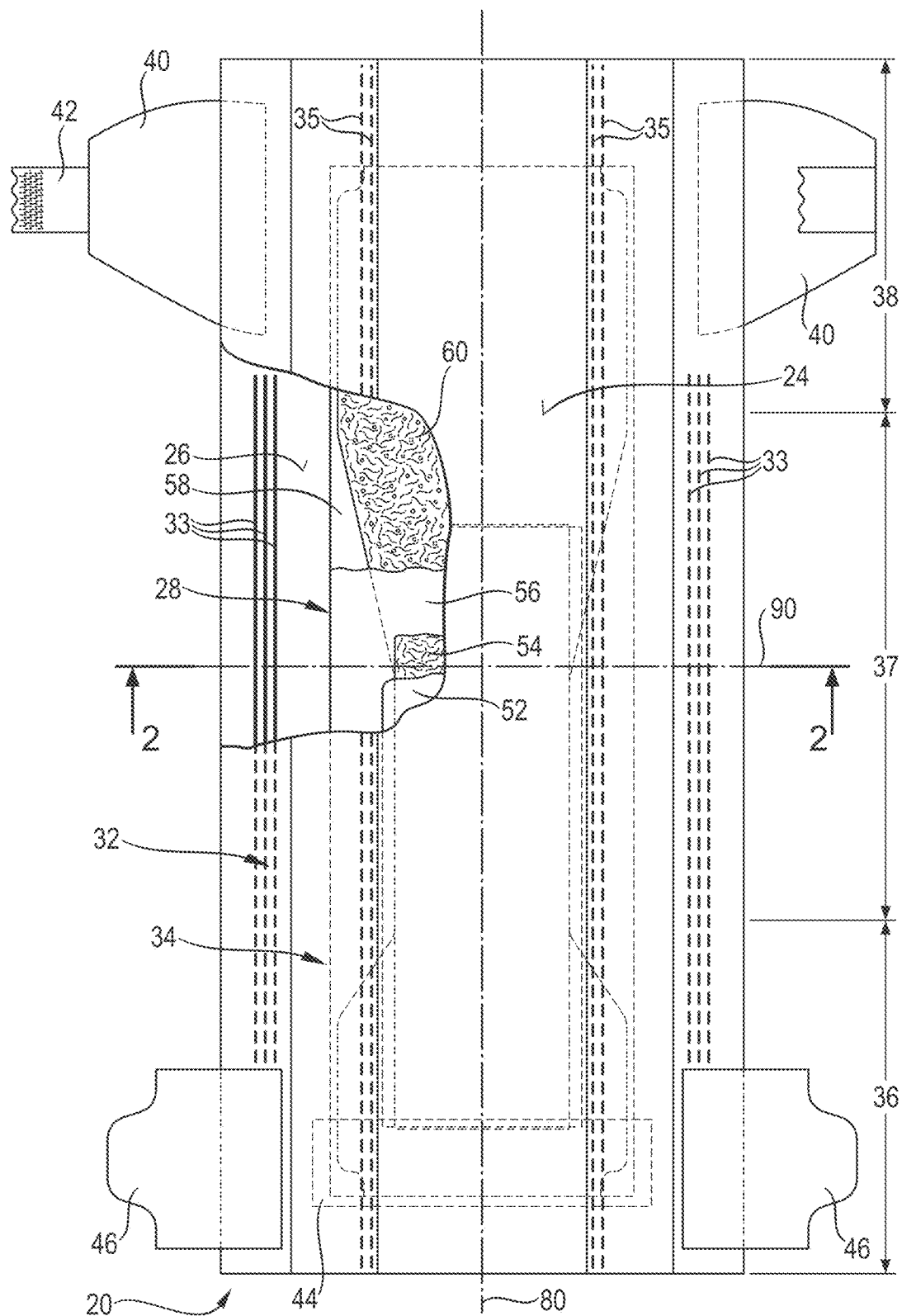
FIG. 1 is a top view of an exemplary absorbent article in the form of a diaper, which may comprise the agglomerated superabsorbent polymer particles of the present invention, with some layers partially removed.

"Absorbent article" refers to devices that absorb and contain body exudates, particularly urine and other water-containing liquids, and, more specifically, refers to devices that are placed against or in proximity to the body of the wearer to absorb and contain the various exudates discharged from the body. Absorbent articles may include diapers (diapers for babies and infants and diapers to address adult incontinence), pants (pants for babies and infants and pants to address adult incontinence), disposable absorbent inserts for diapers and pants having a re-usable outer cover), feminine care absorbent articles such as sanitary napkins or pantiliners, breast pads, care mats, bibs, wipes, and the like. As used herein, the term "exudates" includes, but is not limited to, urine, blood, vaginal discharges, breast milk, sweat and fecal matter. Preferred absorbent articles of the present invention are disposable absorbent articles, more preferably disposable diapers, disposable pants and disposable absorbent inserts.

"Absorbent core" is used herein to refer to a structure disposed between a topsheet and backsheet of an absorbent article for absorbing and containing liquid received by the absorbent article.

"Airfelt" is used herein to refer to comminuted wood pulp, which is a form of cellulosic fiber.

"Base polymer particles" as used herein, refers to SAP particles, which have not undergone any surface treatment, such as surface cross-linking and/or surface coating, after having been polymerized and comminuted into superabsorbent polymer particles.

Generally, base polymer particles have higher capacity and lower permeability compared to surface treated SAP particles.

As used herein, the term "degradation" refers to the conversion of SAP into soluble PAA polymers via the actions of de-polymerization, de-crosslinking, molecular backbone breaking, or any combination thereof.

"Disposable" is used in its ordinary sense to mean an article that is disposed or discarded after a limited number of usage events over varying lengths of time, for example, less than 10 events, less than 5 events, or less than 2 events. If the disposable absorbent article is a diaper, a pant, absorbent insert, sanitary napkin, sanitary pad or wet wipe for personal hygiene use, the disposable absorbent article is most often intended to be disposed after single use.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be pre-formed any where along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

"Superabsorbent polymer material" ("SAP material") is used herein to refer to crosslinked polymeric materials that can absorb at least 10 times their weight of an aqueous 0.9% saline solution as measured using the Centrifuge Retention Capacity test set out below. Superabsorbent polymer material of the present invention is made of polyacrylic acid polymers.

"Superabsorbent polymer particles" ("SAP particles") is used herein to refer to superabsorbent polymer material that is in particulate form so as to be flowable in the dry state.

"Pre-existing superabsorbent polymer material" ("pre-existing SAP material") is used herein to refer to SAP material that is not within the scope of the invention but that is material that has been degraded to obtain s-PAA polymers which can be used for the present invention.

"Soluble polyacrylic acid polymers" (hereinafter abbreviated as "s-PAA polymers") are polymers that are soluble in aqueous solutions. They are not cross-linked to be above the gel-point. The "gel point" is an abrupt change in the viscosity of a solution containing a polymer. At the gel point, a solution undergoes gelation, leading to a gel formation, as reflected in a loss in fluidity and the formation of a 3D network (i.e. cross-linked polymer chains).

"% wt", "% w" "weight-%", and "wt %" are used herein interchangeably and all mean "percent weight".

Superabsorbent Polymer Material Comprising Soluble Polyacrylic Acid Polymers

The superabsorbent polymer material of the present invention comprises cross-linked poly(meth)acrylic acid and salts thereof (hereinafter simply referred to as "polyacrylic acid"), and further comprises s-PAA polymers. The cross-linked polyacrylic acid thereof have an average distance $R_{xl}$ between neighboring crosslinks, and the soluble polyacrylic acid polymers have an average diameter of gyration $2*R_g$. The ratio of $2*R_g$ to $R_{xl}$ is at least 1.1, or at least 1.2, or at least 1.25, or at least 1.3, or at least 1.4, or at least 1.5. The ratio of $2*R_g$ to $R_{xl}$ may not be more than 5.0, or not more than 4.5, or not more than 4.0, or not more than 3.5, or not more than 3.0, or not more than 2.5.

The s-PAA polymers may have a weight average molecular weight $M_w$ of from 250 kDa to 3 MDa, or from 300 kDa to 2 MDa, or from 300 kDa to 1 MDa.

The weight average molecular weight $M_w$ inter alia influences the diameter of gyration of the s-PAA polymers. Higher weight average molecular weight $M_w$ will typically result in a higher diameter of gyration. However, there are other factors which also impact the diameter of gyration of the s-PAA polymers, especially whether the s-PAA polymers are linear or branched, and, if the s-PAA polymers are branched, the degree of branching (number of branches and length of the polymer chains within the branches). Generally, branched polymers have a lower diameter of gyration than linear polymers, and polymers with higher degree of branching having lower diameter of gyration than polymers with relatively lower degree of branching.

S-PAA polymers having a weight average molecular weight of below 250 kDa, may negatively impact the amount of extractables, and deteriorate the properties of the SAP material, such as capacity (as defined by CRC) and permeability (as defined by UPM). Lower weight average molecular weight means smaller molecule size, which increases the risk of the s-PAA polymers leaking out of the SAP material upon absorption of liquid and swelling of the material.

By choosing s-PAA polymers having a weight average molecular weight $M_w$ of more than 3 MDa, the viscosity of the polyacrylic acid polymers in solution increases, which negatively impacts the processability. Furthermore, an excessively high weight average molecular weight means that very large polymers are comprised by the SAP material, which may negatively affect the performance of the SAP material, given the polyacrylic acid polymers do not get, or only to a very small degree, polymerized into the cross-linked polyacrylic acid network of the SAP material. Consequently, a relatively large proportion of the overall weight of the SAP material cannot meaningfully contribute to the absorption properties, such as CRC and UPM.

Interestingly, it has been found that when s-PAA polymers derived by degradation of pre-existing SAP material are used for incorporation into (new) SAP material, s-PAA polymers of lower weight average molecular weight $M_w$ can be used compared to s-PAA polymers made from virgin acrylic acid monomers.

It is believed that s-PAA polymers derived by degradation of pre-existing SAP material, such as pre-existing SAP particles, have a higher degree of branching, i.e. there are more intersections at which a polymer chain branches out into two polymer chains (not to be confused with a cross-link, which bonds two pre-existing polymer chains to each other, forming a cross-link). Compared thereto, s-PAA polymers polymerized from virgin acrylic acid polymers is linear or at least branched to a very small extent. S-PAA polymers with higher degree of branching will adopt a different three-dimensional configuration within the SAP material, especially when the SAP material starts to swell.

If the s-PAA polymers comprised by the SAP material of the present invention are derived from degradation of pre-existing SAP material, such as pre-existing SAP particles, the pre-existing SAP material can be pre-existing virgin SAP material, pre-existing post-consumer recycled SAP material, pre-existing post-industrial recycled SAP material, or a combination of those materials. "Post-consumer recycled SAP material", as used herein, refer to pre-existing SAP material which has been comprised by an absorbent article and the absorbent article has been used by a consumer (e.g. worn by an incontinent user). After use, the absorbent article is recycled, and the pre-existing post-consumer recycled SAP material is isolated from the absorbent article and is degraded into s-PAA polymers. "Post-industrial recycled SAP material", as used herein, refer to pre-existing SAP material which may or may not have been comprised by an absorbent article. The post-industrial recycled SAP material has not been previously used, e.g. it was not comprised by an absorbent article which has been used by a consumer. Instead, the post-industrial recycled SAP material may be derived from absorbent articles which have been sorted out during production, e.g. because they were defective. The post-industrial recycled SAP material which was not comprised by absorbent articles may have been sorted out during production of the previous SAP material, e.g. because it did not meet the required performance targets (such as capacity, whiteness or the like).

The s-PAA polymers may be present throughout the SAP material, i.e. the presence of the s-PAA polymers may not be confined to the surface of the SAP material (e.g. to the surface of SAP particles). Thus, the s-PAA polymers are not intended to be applied as a surface treatment of the SAP material or the like.

If the SAP material is in the form of SAP particles, the SAP particles may be of numerous shapes. The term "particles" refers to granules, fibers, flakes, spheres, powders, platelets and other shapes and forms known to persons skilled in the art of SAP particles. In some embodiments, the SAP particles can be in the shape of fibers, i.e. elongated, acicular superabsorbent polymer particles. In those embodiments, the SAP particles fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

Alternatively, the SAP particles of the present invention are spherical-like particles. According to the present invention and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. In such embodiments, the SAP particles may have a particle size of less than 850 μm, or from 50 to 850 μm, preferably from 100 to 500 μm, more preferably from 150 to 300 μm, as measured according to EDANA method WSP 220.2-05. SAP particles having a relatively low particle size help to increase the surface area which is in contact with liquid exudates and therefore support fast absorption of liquid exudates.

The superabsorbent polymer material may be partially neutralized, e.g. by polymerizing the acrylic acid monomers at 40 mol % to 95 mol % neutralization, or at 50 mol % to 80 mol % neutralization, or at 55 mol % to 75 mol % neutralization. The superabsorbent polymer material may alternatively, or in addition, be neutralized after polymerization, such that the total degree of neutralization is 40-95 mol %, or 50-80 mol %, or 55-75 mol %.

The term "surface" describes the outer-facing boundaries of the particle. For porous SAP particles, exposed internal surfaces may also belong to the surface. The term "surface cross-linked SAP particle" refers to an SAP particle having its molecular chains present in the vicinity of the particle surface cross-linked by a compound referred to as surface cross-linker. The surface cross-linker is applied to the surface of the particle. In a surface cross-linked SAP particle, the level of cross-links in the vicinity of the surface of the SAP particle is generally higher than the level of cross-links in the interior of the SAP.

Commonly applied surface cross-linkers are thermally activatable surface cross-linkers. The term "thermally activatable surface cross-linkers" refers to surface cross-linkers, which only react upon exposure to increased temperatures, typically around 150° C. Thermally activatable surface cross-linkers known in the prior art are e.g. di- or polyfunctional agents that are capable of building additional cross-links between the polymer chains of the SAPs. Examples of thermally activatable surface cross-linkers include but are not limited to: di- or polyhydric alcohols, or derivatives thereof, capable of forming di- or poly-hydric alcohols, alkylene carbonates, ketales, and di- or polyglycidlyethers, haloepoxy compounds, polyaldehydes, polyoles and polyamines. The cross-linking is based on a re-action between the functional groups comprised by the polymer, for example, an esterification reaction between a carboxyl group (comprised by the polymer) and a hydroxyl group (comprised by the surface cross-linker). As typically a relatively large fraction of the carboxyl groups of the polymer chain is neutralized prior to the polymerization step, commonly only few carboxyl groups are available for this surface cross-linking process known in the art. E.g. in a 70% percent neutralized polymer only 3 out of 10 carboxylic groups are available for covalent surface cross-linking.

The surface of the SAP particles may be coated, either instead of being surface cross-linked or, more preferably, in addition to being surface crosslinked (wherein coating is carried out after surface cross-linking). The coating makes the surface sticky so that SAP particles cannot rearrange (so they cannot block voids) easily upon wetting.

For example, the SAP particles may be coated with a cationic polymer. Preferred cationic polymers can include polyamine or polyimine materials which are reactive with at least one component included in body fluids, especially in urine. Preferred polyamine materials are selected from the group consisting of (1) polymers having primary amine groups (e.g., polyvinylamine, polyallyl amine); (2) polymers having secondary amine groups (e.g., polyethyleneimine); and (3) polymers having tertiary amine groups (e.g., poly N, N-dimethylalkyl amine). Practical examples of the cationic polymer are, for example, polyethyleneimine, a modified polyethyleneimine which is crosslinked by epihalohydrine in a range soluble in water, polyamine, a modified polyamidoamine by graft of ethyleneimine, polyetheramine, polyvinylamine, polyalkylamine, polyamidopolyamine, and polyallylamine.

A cationic polymer coated on the surface of the SAP particle may have a weight-average molecular weight $M_w$ of at least 500 Da, more preferably 5,000 Da, most preferably 10,000 Da or more. Cationic polymers having a weight-average molecular weight of more than 500 or more are not limited to polymers showing a single maximum value (a peak) in a molecular weight analysis by gel permeation chromatography, and polymers having a weight-average molecular weight of 500 or more may be used even if it exhibits a plural maximum value (peaks).

A preferable amount of the cationic polymer is in a range of from about 0.05 to 20 parts by weight against 100 parts by weight of the superabsorbent polymer particle, more preferably from about 0.3 to 10 parts by weight, and most preferably from about 0.5 to 5 parts by weight.

The s-PAA polymers may be comprised by the SAP material in an amount of up to 50.0% by weight, or up to 40.0% by weight, or up to 30.0% by weight, or up to 25.0%, or up to 20.0% by weight based on the total weight of the SAP material. Such amounts have been found to not negatively impact the performance properties of the SAP material, such as capacity (measured as CRC) and permeability (measured as permeability).

The s-PAA polymers may be comprised by the SAP material in an amount of at least 3.0% by weight, or at least 5.0% by weight, or at least 7.5% by weight, or at least 10.0% by weight based on the total weight of the SAP material.

The SAP material of the invention, comprising s-PAA polymers having a weight average molecular weight of from 250 kDa to 3 MDa, has been found to have good performance properties which make it useful for incorporation in absorbent articles.

The SAP material of the invention may have an amount of extractables of less than 15% wt, or less than 12% wt or less than 11% wt. The amount of extractables generally increases if the capacity of the SAP material increases. The SAP materials of the invention may have a ratio of amount of extractables (weight-%) to capacity (g/g) to less than 0.30, or less than 0.25.

The SAP material of the present invention may have a capacity of at least 25 g/g, as measured in accordance with the Centrifuge Retention Capacity (CRC) method set out below.

The SAP material of the present invention may have an EFFC value of at least 25 g/g, or at least 25 g/g. The EFFC value combines the capacity (CRC) and the Absorption Against Pressure (AAP) performance of the SAP material as $$EFFC=(CRC+AAP)/2$$

Method of Making the SAP Material Comprising s-PAA Polymers

The SAP material described above can be made by a method wherein SAP material is obtained by polymerizing an aqueous solution comprising the steps of:
 a) providing an aqueous solution of polymerizable acrylic acid monomers and/or polymerizable acrylic acid oligomers, optionally neutralizing at least some of the polymerizable acrylic acid monomers and/or polymerizable acrylic acid oligomers;
 b) optionally providing one or more ethylenically unsaturated co-monomers, optionally neutralizing at least some of the ethylenically unsaturated co-monomer of step b);
 c) providing one or more crosslinker(s);
 d) providing one or more initiator(s);
 e) providing at least 3 weight-% of soluble polyacrylic acid polymers based on the total weight of the soluble polyacrylic acid polymers provided in step e) and the monomers, oligomers, co-monomers, crosslinkers and initiators provided in steps a) to d)
 f) mixing the aqueous solution of monomers, oligomers, co-monomers, crosslinkers and initiators and soluble polyacrylic acid polymers provided in steps a) to e); and
 g) polymerizing the mixture obtained in step f) to obtain a superabsorbent polymer material.

As it can be assumed that all components provided in steps a) to e) react in the polymerization, the weight-% of step e) is the same as the weight-% of s-PAA polymers in the superabsorbent polymer material obtained by the method.

When providing the s-PAA polymers in method step e) the s-PAA polymers may be provided to the aqueous solution in dry form (as powder) or may be provided as aqueous solution. As s-PAA polymers are often hard to dissolve, it may indeed be beneficial to provide the s-PAA polymers as aqueous solution. Moreover, if the s-PAA polymers are obtained from degradation of pre-existing post-consumer recycled SAP material, the degradation product (i.e. the s-PAA polymers) would most likely be an aqueous solution, so drying and re-dissolving the s-PAA polymers would be time- and energy-consuming.

The s-PAA polymers may be provided at weight-percent of up to 50.0%, or up to 40.0%, or up to 30.0%, or up to 25.0%, or up to 20.0% based on the total weight of the soluble polyacrylic acid polymers provided in step e) and the monomers and oligomers provided in method step a).

The SAP material may be dried after polymerization. The SAP material may also be comminuted to obtain SAP particles. Comminuting may be done subsequent to drying or may be done prior to drying (e.g. by so-called wet grinding).

The ethylenically unsaturated co-monomers provided in method step b) may be water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable ethylenically unsaturated co-monomers provided in method step b) are, for example, ethylenically unsaturated carboxylic acids, such as methacrylic acid and itaconic acid.

Further suitable monomers ethylenically unsaturated co-monomers provided in method step b) are, for example, ethylenically unsaturated sulfonic acids, such as styrenesulfonic acid.

Other ethylenically unsaturated co-monomers that may be added in combination with acrylic acid, methacrylic acid, itaconic acid or ethylenically unsaturated sulfonic acids, are styrenesulfonic acid copolymerizable with the ethylenically unsaturated monomers provided in method step a) are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, and/or diethylaminoethyl methacrylate.

The acid groups of the monomers a) and/or co-comonomers b) may have been partly neutralized. The neutralization can be conducted at the monomer stage. This can typically be accomplished by mixing in the neutralizing agent as an aqueous solution or else preferably as a solid. The degree of neutralization may preferably be from 40 to 95 mol %, more preferably from 40 to 80 mol % and most preferably from 50 to 75 mol %. A customary neutralizing agent can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

Suitable crosslinkers provided in method step b) are compounds having at least two groups suitable for crosslinking. Such groups are, for example, ethylenically unsaturated groups which can be polymerized free-radically into the polymer chain, and functional groups which can form covalent bonds with the acid groups of the monomer provided in method step a) and/or with the co-monomers provided in method step b). In addition, polyvalent metal salts which can form coordinate bonds with at least two acid groups of the monomer provided in method step a) are also suitable as crosslinkers.

The crosslinkers provided in method step c) are preferably compounds having at least two polymerizable groups which can be polymerized free-radically into the polymer network. Suitable crosslinkers provided in method step b) are, for example, methylenebisacrylamide, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, or mixed acrylates which, as well as acrylate groups, comprise further ethylenically unsaturated groups.

The amount of crosslinker provided in method step c) is preferably 0.0001% to 0.5% by weight, more preferably 0.001% to 0.2% by weight and most preferably 0.01% to 0.1% by weight, based on the total weight of the un-neutralized monomer provided in method step a) and un-neutralized co-comonomers provided in step b).

Initiators provided in method step d) may be all compounds which generate free radicals under the polymerization conditions, for example thermal initiators, redox initiators or photoinitiators.

Suitable redox initiators are potassium peroxodisulfate or sodium peroxodisulfate/ascorbic acid, hydrogen peroxide/ascorbic acid, potassium peroxodisulfate or sodium peroxodisulfate/sodium bisulfite and hydrogen peroxide/sodium bisulfite. Preferably, mixtures of thermal initiators and redox initiators are used, such as potassium peroxodisulfate or sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures can be obtained as Brüggolite® FF6 and Brüggolite® FF7 (Brüggemann Chemicals; Heilbronn; Germany).

Suitable thermal initiators are especially azo initiators, such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4"-azobis(4-cyanopentanoic acid), 4,4' and the sodium salts thereof, 2,2'-azobis[2-methyl-N-(2-hydroxyethyl)propionamide] and 2,2'-azobis(imino-1-pyrrolidino-2-ethylpropane) dihydrochloride.

Suitable photoinitiators are, for example, 2-hydroxy-2-methylpropiophenone and 1-[4-(2-hydroxyethoxy)phenyl]-2-hydroxy-2-methyl-1-propan-1-one.

Mixing and polymerization of method steps f) and g) may be done in a kneading reactor or belt reactor. In the kneading reactor, the polymer gel formed in the polymerization is comminuted continuously by, for example, contra-rotatory stirrer shafts. Polymerization in a belt reactor is also well known in the art. Polymerization in a belt reactor forms a polymer gel which has to be comminuted in a further process step, for example in an extruder or kneader.

The surface crosslinking may be performed in such a way that a solution, such as an aqueous solution, of the surface crosslinker is sprayed onto the dried SAP particles. After the spray application, the surface crosslinker-coated polymer particles are thermally surface crosslinked.

Spray application of a solution of the surface crosslinker onto the SAP particles is preferably performed in mixers with moving mixing tools, such as screw mixers, disk mixers and paddle mixers.

Absorbent Articles

Figure 2:
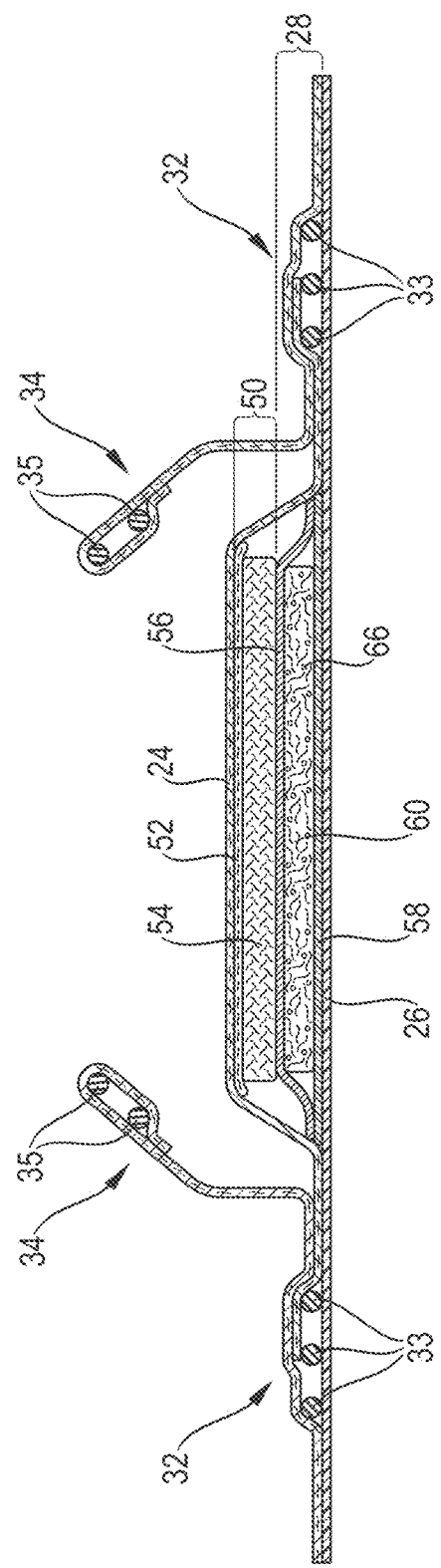
FIG. 2 is a transversal cross-section of the diaper of FIG. 1.

A typical disposable absorbent article, in which SAP material of the present invention can be used, is placed against or in proximity to the body of the wearer to absorb and contain the various exudates discharged from the body and is represented in FIGS. 1 and 2 in the form of a diaper 20.

In more details, FIG. 1 is a plan view of an exemplary diaper 20, in a flat-out state, with portions of the diaper being cut-away to more clearly show the construction of the diaper 20. This diaper 20 is shown for illustration purpose only as the SAP material of the present invention may be comprised in a wide variety of diapers or other absorbent articles.

As shown in FIGS. 1 and 2, the absorbent article, here a diaper, can comprise a liquid pervious topsheet 24, a liquid impervious backsheet 26, an absorbent core 28 which is positioned between f the topsheet 24 and the backsheet 26. The absorbent core 28 can absorb and contain liquid received by the absorbent article and may comprise absorbent materials 60, such as the SAP material of the present invention 66 and/or cellulose fibers, as well as other absorbent and non-absorbent materials commonly used in absorbent articles (e.g. thermoplastic adhesives immobilizing the SAP particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), SAP material (such as SAP particles) disposed on the one or more substrate layers, and a thermoplastic composition typically disposed on the SAP material (such as SAP particles). Typically, the thermoplastic composition is a thermoplastic adhesive material. In one embodiment, the thermoplastic adhesive material forms a fibrous layer which is at least partially in contact with the SAP material (such as SAP particles) on the one or more substrate layers and partially in contact with the one or more substrate layers. Auxiliary adhesive might be deposited on the one or more substrate layers before application of the SAP material (such as SAP particles) for enhancing adhesion of the SAP material (e.g. SAP particles) and/or of the thermoplastic adhesive material to the respective substrate layer(s). The absorbent core may also include one or more cover layer(s) such that the SAP material (e.g. SAP particles) are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the SAP material (e.g., SAP particles), the thermoplastic composition, optionally the auxiliary adhesive, optionally the cover layer(s), and optionally odor control compounds.

The absorbent core may also comprise a mixture of SAP particles and airfelt, which may be enwrapped within one or more substrate layers, such as nonwoven webs or paper tissue. Such absorbent cores may comprise from 30% to 95%, or from 50% to 95% of SAP particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of SAP particles by weight of the absorbent material.

The absorbent core may comprise mixtures or combinations of the SAP material of the present invention and other SAP materials (such as other SAP particles, and/or SAP foams). For example, the absorbent core may comprise at least 50%, or at least 60%, or at least 70%, or at least 80%, or at least 90% or 100% of SAP material by weight of the absorbent material, wherein the SAP material comprise at least 10%, or at least 20% or at least 30% or at least 50%, or at least 75%, or at least 90%, or 100% by weight of the SAP material of the present invention based on the total weight of SAP material in the absorbent core.

The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet.

The ADS may be free of SAP material. The prior art discloses many types of acquisition-distribution systems, see for example WO2000/59430, WO95/10996, 1145700254, WO02/067809. However, the SAP material of the present invention may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90%, or 100% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 1 and 2. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Bio-Based Materials

Absorbent articles comprising the SAP material of the present invention, may comprise a bio-based content value from about 10% to about 100% using ASTM D6866-10, method B, or from about 25% to about 75%, or from about 50% to about 60%.

The various components of the absorbent article, such as the topsheet, the backsheet, the fasteners, the ADS, the back ears, the outer cover nonwoven, an elastic laminate (such as the elastic laminate forming a belt of an absorbent article), or any other component, may comprise a bio-based content value from about 10% to about 100% using ASTM D6866-10, method B, or from about 25% to about 75%, or from about 50% to about 60%.

In order to apply the methodology of ASTM D6866-10 to determine the bio-based content of a single component material (i.e. a nonwoven), that material is isolated and cleaned such that the resulting specimen reflects the constituent starting material as closely as possible. For example, if a component needs to be deconstructed (e.g. removal elastic strands removed from a laminate formed of one or more nonwovens and elastic strands) the nonwoven is washed with an appropriate solvent so as to remove any residual adhesive present. In order to apply the methodology of ASTM D6866-10 to a sample assembly of two or more materials of differing or unknown compositions, the sample is homogenized by grinding the material into particulate form (with particle size of about 20 mesh or smaller) using known grinding methods (such as with a Wiley grinding mill). A representative specimen of suitable mass is then taken from the resulting sample of randomly mixed particles.

Validation of Polymers Derived From Renewable Resources

A suitable validation technique is through 14C analysis. A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized to carbon dioxide. This radioactive isotope represents a small but measurable fraction of atmospheric carbon. Atmospheric carbon dioxide is cycled by green plants to make organic molecules during photosynthesis. The cycle is completed when the green plants or other forms of life metabolize the organic molecules, thereby producing carbon dioxide which is released back to the atmosphere. Virtually all forms of life on Earth depend on this green plant production of organic molecules to grow and reproduce. Therefore, the 14C that exists in the atmosphere becomes part of all life forms, and their biological products. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the bio-based content of materials can be determined. ASTM International, formally known as the American Society for Testing and Materials, has established a standard method for assessing the bio-based content of materials. The ASTM method is designated ASTM D6866-10.

The application of ASTM D6866-10 to derive a "bio-based content" is built on the same concepts as radiocarbon dating, but without use of the age equations. The analysis is performed by deriving a ratio of the amount of organic radiocarbon (14C) in an unknown sample to that of a modern reference standard. The ratio is reported as a percentage with the units "pMC" (percent modern carbon).

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, for example, it would give a radiocarbon signature near 54 pMC (assuming the petroleum derivatives have the same percentage of carbon as the soybeans).

A biomass content result is derived by assigning 100% equal to 107.5 pMC and 0% equal to 0 pMC. In this regard, a sample measuring 99 pMC will give an equivalent bio-based content value of 92%.

Assessment of the materials described herein can be done in accordance with ASTM D6866. The mean values quoted in this report encompasses an absolute range of 6% (plus and minus 3% on either side of the bio-based content value) to account for variations in end-component radiocarbon signatures. It is presumed that all materials are present day or fossil in origin and that the desired result is the amount of biobased component "present" in the material, not the amount of biobased material "used" in the manufacturing process.

Test Methods

Gel Permeation Chromatography with Multi-Angle Light Scattering and Refractive Index Detection (GPC-MALS/RI) for Polymer Molecular Weight Distribution Measurement Gel Permeation Chromatography (GPC) with Multi-Angle Light Scattering (MALS) and Refractive Index (RI) Detection (GPC-MALS/RI) permits the measurement of absolute weight average molecular weight $M_w$ of a polymer without the need for column calibration methods or standards. The GPC system allows molecules to be separated as a function of their molecular size. MALS and RI allow information to be obtained on the number average (Mn) and weight average (Mw) molecular weight. The $M_w$ distribution of water-soluble polymers, such as s-PAA polymers, is typically measured by using a Liquid Chromatography system consisting generally of a pump system, an autosampler (e.g., Agilent 1260 Infinity pump system with OpenLab Chemstation software, Agilent Technology, Santa Clara, CA, USA), and a column set of appropriate dimensions (e.g., Waters ultrahydrogel guard column, 6 mm ID×40 mm length, two ultrahydrogel linear columns, 7.8 mm ID×300 mm length, Waters Corporation of Milford, Mass., USA) which is typically operated at 40° C.

The column set comprises one or typically more subsequently connected columns with varying pore-sizes graded for different molecular weight polymers and columns are generally selected such to provide resolution of wide and relevant molecular weights range.

Commonly, the mobile phase is for example 0.1M sodium nitrate in water containing 0.02% sodium azide and is pumped at a flow rate of about 1 mL/min, isocratically. A multiangle light scattering (MALS) detector (e.g. DAWN®) and a differential refractive index (RI) detector (e.g. Wyatt Technology of Santa Barbara, Calif., USA) controlled by respective software packages, e.g. Wyatt Astra®, are used. A sample is typically prepared by dissolving polymer materials, such as s-PAA polymers, in the mobile phase at about 1 mg per ml and by mixing the solution for overnight hydration at room temperature. The sample is filtered through a membrane filter (e.g. a 0.8 μm Versapor filter, PALL, Life Sciences, NY, USA) into the LC autosampler vial using a syringe before the GPC analysis.

A dn/dc (differential change of refractive index with concentration) value is typically measured on the polymer materials of interest and used for the number average molecular weight and weight average molecular weights determination by the respective detector software.

Urine Permeability Measurement (UPM) Test Method
Lab Conditions:

This test has to be performed in a climate conditioned room at standard conditions of 23° C.±2° C. temperature and 45%±10% relative humidity.

Urine Permeability Measurement System

This method determined the permeability of a swollen hydrogel layer 1318. The equipment used for this method is described below. This method is closely related to the SFC (Saline Flow Conductivity) test method of the prior art.

Figure 3:
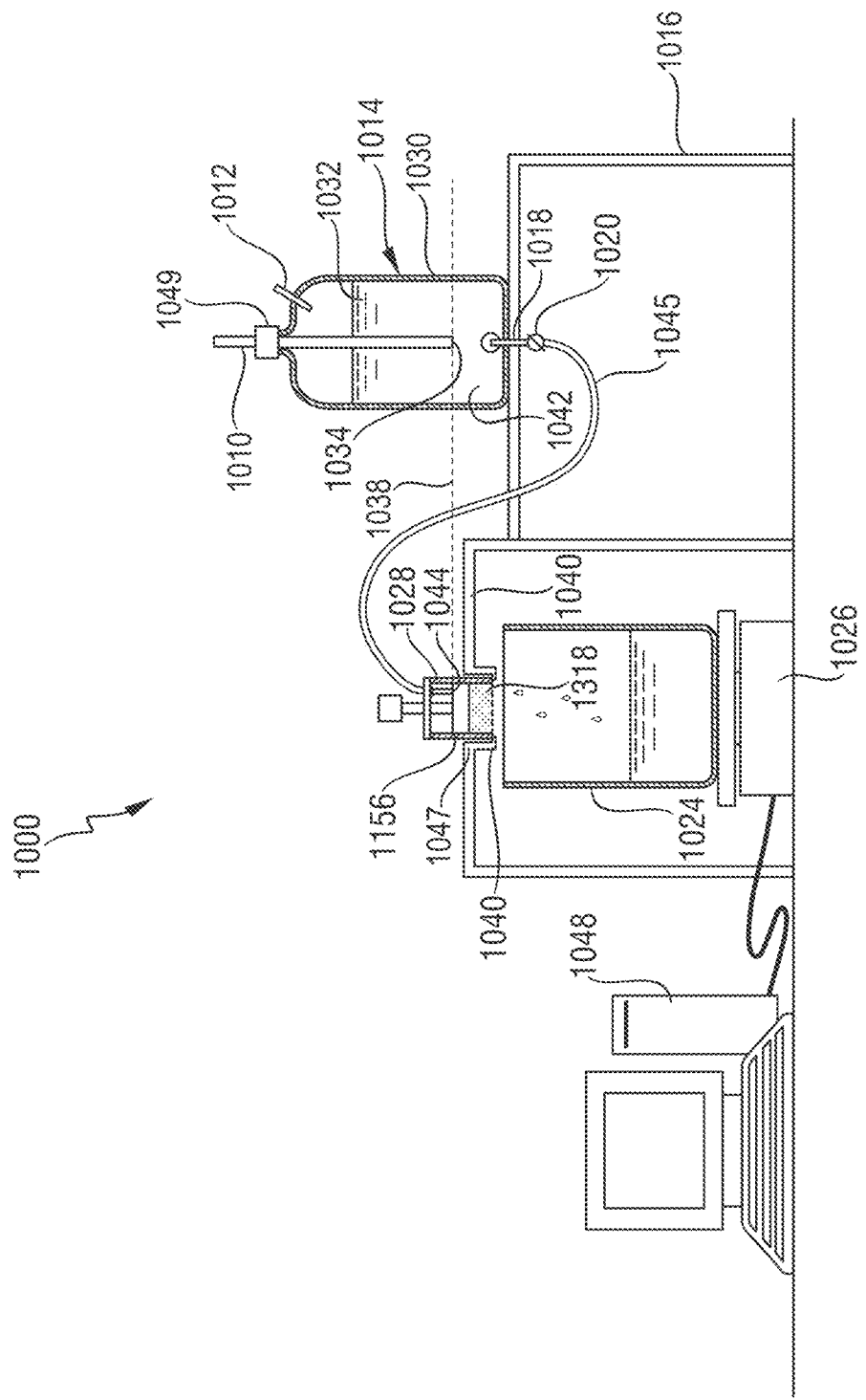
FIG. 3 is a partial cross-sectional side view of a suitable permeability measurement system for conducting the Urine Permeability Measurement Test.

FIG. 3 shows permeability measurement system 1000 set-up with the constant hydrostatic head reservoir 1014, open-ended tube for air admittance 1010, stoppered vent for refilling 1012, laboratory reck 1016, delivery tube 1018 with flexible tube 1045 with Tygon tube nozzle 1044, stopcock 1020, cover plate 1047 and supporting ring 1040, receiving vessel 1024, balance 1026 and piston/cylinder assembly 1028.

Figure 4:
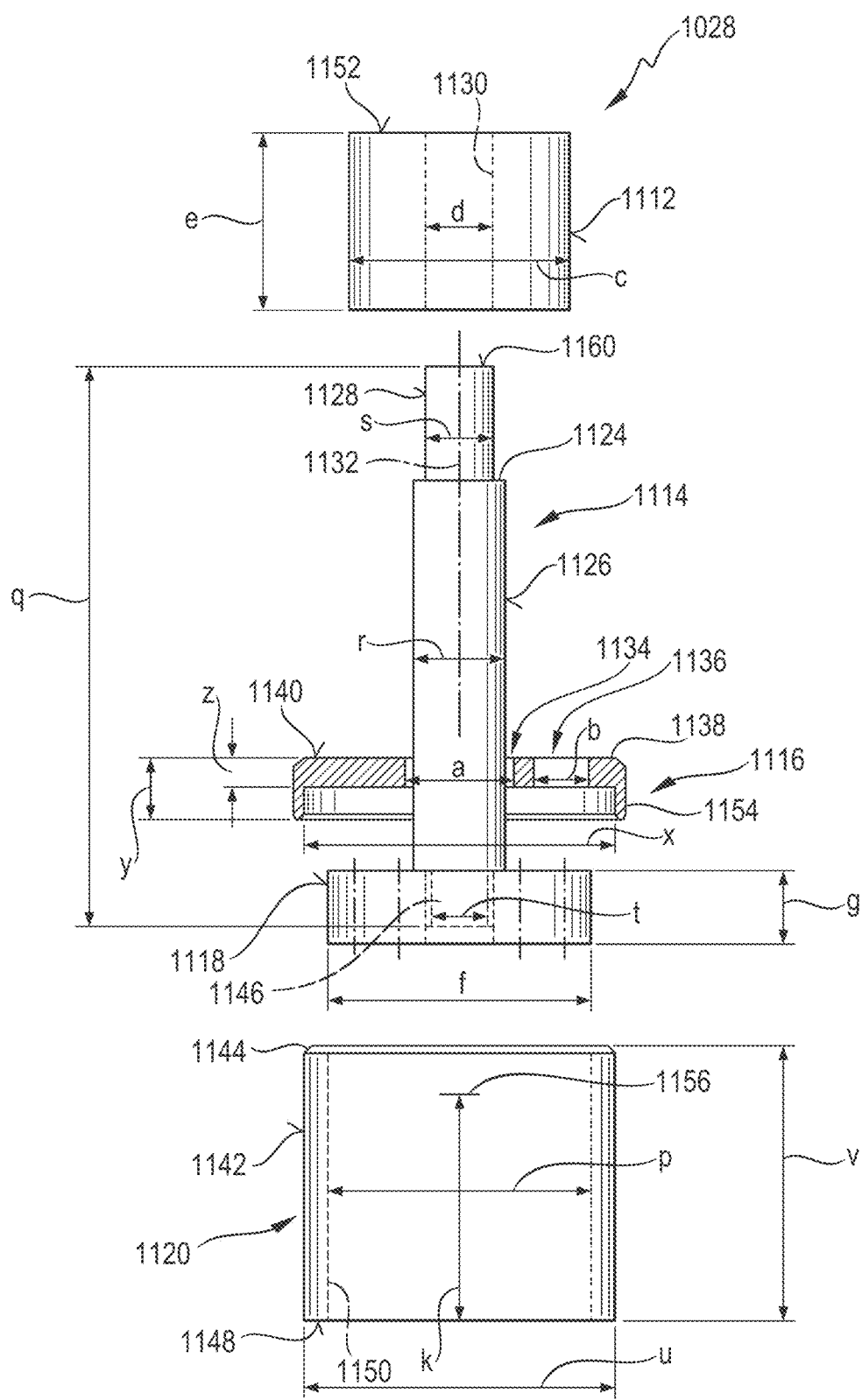
FIG. 4 is a cross-sectional side view of a piston/cylinder assembly for use in conducting the Urine Permeability Measurement Test.
Figure 5:
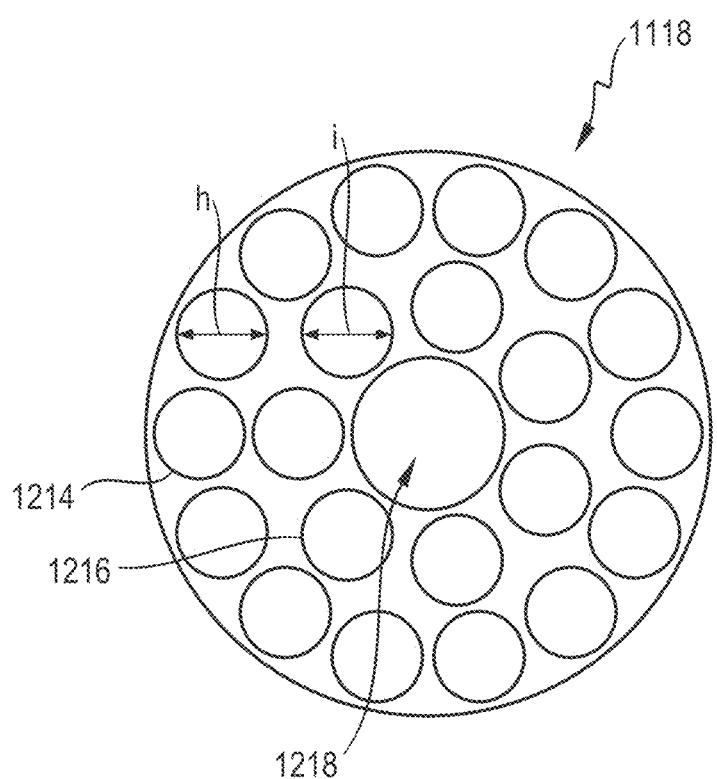
FIG. 5 is a top view of a piston head suitable for use in the piston/cylinder assembly shown in FIG. 4.

FIG. 4 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a stainless-steel screen cloth (ISO 9044 Material 1.4401, mesh size 0.038 mm, wire diameter 0.025 mm) (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 22.15 (±0.02) mm. An upper portion 1128 of the piston shaft 1114 has a diameter s of 15.8 mm, forming a shoulder 1124. A lower portion 1146 of the piston shaft 1114 has a diameter t of approximately ⅝ inch (15.9 mm) and is threaded to screw firmly into the center hole 1218 (see FIG. 5) of the piston head 1118. The piston head 1118 is perforated, made of transparent polycarbonate (e.g., Lexan®), and is also screened with a stretched stainless-steel screen cloth (ISO 9044 Material 1.4401, mesh size 0.038 mm, wire diameter 0.025 mm) (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the inner area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be repositioned with the same orientation relative to one another for each measurement.

The cylinder 1120 specification details are:
Outer diameter u of the Cylinder 1120: 70.35 mm (±0.05 mm)
Inner diameter p of the Cylinder 1120: 60.0 mm (±0.05 mm)
Height v of the Cylinder 1120: 60.5 mm. Cylinder height must not be lower than 55.0 mm!

The cylinder lid 1116 specification details are:
Outer diameter w of cylinder lid 1116: 76.05 mm (±0.05 mm)
Inner diameter x of cylinder lid 1116: 70.5 mm (±0.05 mm)
Thickness y of cylinder lid 1116 including lip 1154: 12.7 mm Thickness z of cylinder lid 1116 without lip 1154: 6.35 mm
Diameter a of first lid opening 1134: 22.25 mm (±0.02 mm)
Diameter b of second lid opening 1136: 12.7 mm (±0.1 mm)
Distance between centers of first and second lid openings 1134 and 1136: 23.5 mm The weight 1112 specification details are:
Outer diameter c: 50.0 mm
Diameter d of center bore 1130: 16.0 mm
Height e: 39.0 mm The piston head 1118 specification details are:
Diameter f: 59.7 mm (±0.05 mm)
Height g: 16.5 mm. Piston head height must not be less than 15.0 mm.
Outer holes 1214 (14 total) with a 9.30 (±0.25) mm diameter h, outer holes 1214 equally spaced with
centers being 23.9 mm from the center of center hole 1218.
Inner holes 1216 (7 total) with a 9.30 (±0.25) mm diameter i, inner holes 1216 equally spaced with centers being 13.4 mm from the center of center hole 1218.
Center hole 1218 has a diameter j of approximately ⅝ inches (15.9 mm) and is threaded to accept a lower portion 1146 of piston shaft 1114.

Prior to use, the stainless-steel screens (not shown) of the piston head 1118 and cylinder 1120 should be inspected for clogging, holes or over-stretching and replaced when necessary. A urine permeability measurement apparatus with damaged screen can deliver erroneous UPM results and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the cover plate 1047 and supporting ring 1040 (with circular inner opening of not less than 64 mm diameter) above the receiving vessel 1024.

The cover plate 1047 and supporting ring 1040 are parts as used in the equipment used for the method "K(t) Test Method (Dynamic Effective Permeability and Uptake Kinetics Measurement Test method)" as described in EP 2 535 027 A1 and is called "Zeitabhängiger Durchlässigkeitsprüfstand" or "Time Dependent Permeability Tester", Equipment No. 03-080578 and is commercially available at BRAUN GmbH, Frankfurter Str. 145, 61476 Kronberg, Germany. Upon request, detailed technical drawings are also available.

Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 connected to a flexible tube 1045 (e.g. Tygon tube, capable to connect nozzle and reservoir outlet) and to a Tygon tube nozzle 1044 (inner diameter at least 6.0 mm, length appr. 5.0 cm) for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of approximately 12 mm, but not less than 10.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery flexible tube 1045 is dimensioned (e.g. outer diameter 10 mm) to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar 1049. The constant hydrostatic head reservoir 1014 can be positioned on a laboratory reck 1016 at a suitable height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 2.6 g/sec for at least 10 minutes.

The piston/cylinder assembly 1028 is positioned on the supporting ring 1040 in the cover plate 1047 or suitable alternative rigid stand. The salt solution 1032 passing through the piston/cylinder assembly 1028 containing the swollen hydrogel layer 1318 is collected in a receiving vessel 1024, positioned below (but not in contact with) the piston/cylinder assembly 1028.

The receiving vessel 1024 is positioned on the balance 1026 which is accurate to at least 0.001 g. The digital output of the balance 1026 is connected to a computerized data acquisition system 1048.

Preparation of Reagents (Not Illustrated)

Figure 6:
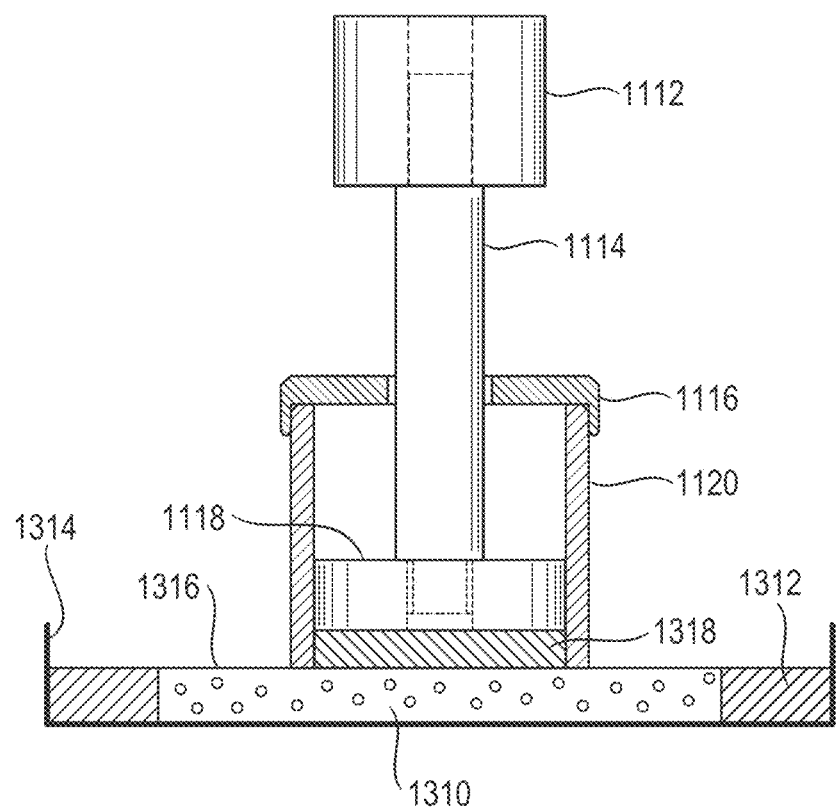
FIG. 6 is a cross-sectional side view of the piston/cylinder assembly of FIG. 4 placed on fritted disc for the swelling phase.

Jayco Synthetic Urine (JSU) 1312 (see FIG. 6) is used for a swelling phase (see UPM Procedure below) and 0.118 M Sodium Chloride (NaCl) Solution 1032 is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4)_2HPO_4$) 0.15 g
Calcium chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, potassium chloride, sodium sulfate, ammonium dihydrogen phosphate, ammonium phosphate (dibasic) and magnesium chloride (or hydrated magnesium chloride) are combined and dissolved in the 80% of distilled water in the 1 L volumetric flask.

Calcium chloride (or hydrated calcium chloride) is dissolved separately in approximately 50 ml distilled water (e.g. in a glass beaker) and the calcium chloride solution is transferred to the 1 L volumetric flask after the other salts are completely dissolved therein. Afterwards, distilled water is added to 1 L (1000 ml±0.4 ml) and the solution is stirred for a few minutes more. Jayco synthetic urine may be stored in a clean plastic container for 10 days. The solution should not be used if it becomes cloudy. 0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask (1000 ml±0.4 ml); and the flask is filled to volume with distilled water. A stir bar is added and the solution is mixed on a stirring plate until all the solids are dissolved.

The conductivity of the prepared Jayco solution must be in the range of appr. 7.48-7.72 mS/cm and of the prepared 0.118 M Sodium Chloride (NaCl) Solution in the range of appr. 12.34-12.66 mS/cm (e.g. measured via COND 70 INSTRUMENT without CELL, #50010522, equipped with Cell VPT51-01 C=0.1 from xs instruments or via LF 320/Set, #300243 equipped with TetraCon 325 from WTW or COND 330i, #02420059 equipped with TetraCon 325 from WTW). The surface tension of each of the solutions must be in the range of 71-75 mN/m (e.g. measured via tensiometer K100 from Kruess with Pt plate).

Test Preparation

Using a solid reference cylinder weight (not shown) (50 mm diameter; 128 mm height), a caliper gauge (not shown) (measurement range 25 mm, accurate to 0.01 mm, piston pressure max. 50 g; e.g. Mitutoyo Digimatic Height Gage) is set to read zero. This operation is conveniently performed on a smooth and level bench (not shown) of at least approximately 11.5 cm×15 cm. The piston/cylinder assembly 1028 without superabsorbent polymer particles is positioned under the caliper gauge (not shown) and a reading, L1, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system 1048. The cover plate 1047 with the supporting ring 1040 is positioned above the receiving vessel 1024.

UPM Procedure 1.5 g (±0.05 g) of superabsorbent polymer particles is weighed onto a suitable weighing paper or weighing aid using an analytical balance. The moisture content of the superabsorbent polymer particles is measured according to the EDANA Moisture Content Test Method NWSP 230.0.R2 (15) or via a Moisture Analyzer (HX204 from Mettler Toledo, drying temperature 130° C., starting superabsorbent polymer particles weight 3.0 g (±0.5 g), stop criterion 1 mg/140 s). If the moisture content of the superabsorbent polymer particles is greater than 3 wt %, then the superabsorbent polymer particles are dried to a moisture level of <3 wt %, e.g. in an oven at 105° C. for 3 h or e.g. at 120° C. for 2 h. Agglomerated superabsorbent polymer particles are dried if moisture level is greater than 5 wt %, e.g. in an oven at 105° C. for 3 h or e.g. at 120° C. for 2 h.

The empty cylinder 1120 is placed on a level benchtop 1046 (not shown) and the superabsorbent polymer particles are quantitatively transferred into the cylinder 1120. The superabsorbent polymer particles are evenly dispersed on the screen (not shown) attached to the bottom 1148 of the cylinder 1120 while rotating the cylinder 1120, e.g. aided by a (manual or electrical) turn table (e.g. petriturn-E or petriturn-M from Schuett). It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The weight 1112 is positioned on the upper portion 1128 of the piston shaft 1114 so that it rests on the shoulder 1124 such that the first and second linear index marks are aligned. The lid 1116 and piston shaft 1126 are then carefully rotated so as to align the third, fourth, fifth, and sixth linear index marks are then aligned with the first and the second linear index marks. The piston head 1118 (via the piston shaft 1114) is then gently lowered to rest on the dry superabsorbent polymer particles. Proper seating of the lid 1116 prevents binding and assures an even distribution of the weight on the hydrogel layer 1318.

Swelling Phase:

A fritted disc of at least 8 cm diameter (e.g. 8-9 cm diameter) and at least 5.0 mm thickness (e.g. 5-7 mm thickness) with porosity "coarse" or "extra coarse" (e.g. Chemglass Inc. # CG 201-51, coarse porosity; or e.g. Robu 1680 with porosity 0) 1310 is placed in a wide flat-bottomed Petri dish 1314 and JSU 1312 is added by pouring JSU 1312 onto the center of the fritted disc 1310 until JSU 1312 reaches the top surface 1316 of the fritted disc 1310. The JSU height must not exceed the height of the fritted disc 1310. It is important to avoid any air or gas bubbles entrapped in or underneath the fritted disc 1310.

The entire piston/cylinder assembly 1028 is lifted and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to ensure the hydrogel layer 1318 does not lose JSU 1312 or take in air during this procedure. The piston/cylinder assembly 1028 is placed under the caliper gauge (not shown) and a reading, L2, is recorded to the nearest 0.01 mm. If the reading changes with time, only the initial value is recorded. The thickness of the hydrogel layer 1318, L0 is determined from L2−L1 to the nearest 0.1 mm.

The piston/cylinder assembly 1028 is transferred to the supporting ring 1040 in the cover plate 1047. The constant hydrostatic head reservoir 1014 is positioned such that the delivery tube nozzle 1044 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer 1048 attached to the balance 1026, the quantity g (in g to accuracy of 0.001 g) of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation.

For each time period of 20 seconds (time $t_{(i-1)}$ to $t_i$) after the initial 60 seconds of the experiment, the respective flow rate $Fs_{(t)}$ (in g/s) and the respective mid-point of the time $t_{(1/2)t}$ (in s) is calculated according to the following formulas:

$$Fs_{(t)} = \frac{(g_{(i-1)} - g_{(i)})}{(t_{(i-1)} - t_{(i)})} \text{ and } t_{(1/2)_t} = \frac{(t_{(i-1)} + t_{(i)})}{2} \quad (XII)$$

The flow rate $Fs_{(t)}$ of each time interval ($t_{(i-1)}$ to $t_i$) is plotted versus the mid-point of the time $t_{(1/2)t}$ of the time interval ($t_{(i-1)}$ to $t_i$). The intercept is calculated as Fs(t=0). Calculation of the Intercept:

The intercept is calculated via a best-fit regression line, e.g. as following: the equation for the intercept of the regression line, a, is:

$$a = y_{AVG} - b \cdot x_{AVG} \quad (XIII)$$

where the slope, b, is calculated as:

$$b = \frac{\sum (x - x_{AVG}) \cdot (y - y_{AVG})}{\sum (x - x_{AVG})^2} \quad (XIV)$$

and where $x_{AVG}$ and $y_{AVG}$ are the sample means AVERAGE of the known_x's and AVERAGE of the known_y's, respectively.

Calculation of Urine Permeability Measurement Q:

The intercept Fs(t=0) is used to calculate Q according to the following formula:

$$Q = \frac{F_s(t=0) \cdot L_0}{\rho \cdot A \cdot \Delta P} \quad (XV)$$

where the flow rate Fs(t=0) is given in g/s, $L_0$ is the initial thickness of the hydrogel layer 1318 in cm, ρ is the density of the salt solution 1032 in g/cm³ (e.g. 1.003 g/cm³ at room temperature). A (from the equation above) is the area of the hydrogel layer 1318 in cm² (e.g. 28.27 cm²), ΔP is the hydrostatic pressure in dyne/cm² (e.g. 4920 dyne/cm²), and the Urine Permeability Measurement, Q, is in units of cm³ sec/g. The average of three determinations should be reported.

| Variable | Description | Unit |
|---|---|---|
| $g_i$ | Mass of salt solution 1032 flown through the swollen gel layer (recorded by the balance) at the time $t_i$ (accuracy 0.001 g) | g |
| $t_i$ | Time point (every 20 s) | s |
| $t_{(1/2)t}$ | Mid-point of time for the respective time interval $t_{i-1}$ to $t_i$ | s |
| $Fs_t$ | Flow Rate at the time interval $t_{i-1}$ to $t_i$ | g/s |
| Fs (t = 0) | Intercept flow rate at t = 0 s from the plot of the flow rate Fs(t) vs. the mid-point of time $t_{(1/2)t}$. | g/s |
| $L_0$ | Thickness of the swollen gel layer (swollen with JSU 1312) before the salt solution 1032 flows through the gel layer. | cm |
| ρ | Density of the salt solution 1032 (1.003 g/cm³) | g/cm³ |
| A | Area of the swollen gel layer (28.27 cm²) | cm² |
| ΔP | Hydrostatic pressure across the gel layer (4920 dyne/cm²) | dyne/cm² |
| Q | Urine Permeability Measurement | cm³ * sec/g |

Capacity is determined according to the Centrifuge Retention Capacity (CRC) test method as set out in EDANA NWSP 241.0.R2(15). In deviation from EDANA NWSP 241.0.R2(15), CRC measurement is started at a lower end of 24.2 g/g (instead of 27.19 g/g as set out in EDANA NWSP 241.0.R2(15).

The Absorption Against Pressure (AAP) test method is set out in EDANA method NWSP 242.0.R2 (15). In deviation from the EDANA method, a pressure of 0.7 psi is applied (instead of a pressure of 0.3 psi provided in EDANA method NWSP 242.0.R2 (15)).

Amount of extractables is measured in accordance with EDANA test method NWSP 270.0.R2 (15). The following deviations from EDANA test method NWSP 270.0.R2 (15) apply herein:

9. Procedure (procedural steps not described below are carried out without deviation from EDANA test method NWSP 270.0.R2 (15):

9.2 Accurately add 200.0±0.1 ml of saline solution to dispenser with a volume of 200 ml (instead of a 250 ml beaker or conical flask as is set out in EDANA test method NWSP 270.0.R2 (15)).

9.4 Add the 0.95 to 1.05 g of a SAP particle sample by weighing it directly into the 250 ml Erlenmeyer flask and add the magnet coin (instead of adding the sample to the weighing vessel or laboratory paper and tare the balance again, as is set out in EDANA test method NWSP 270.0.R2 (15)). Fill the saline solution to the Erlenmeyer flask only at the start of the extraction time.

9.7 Stopper/Cover/Seal the beaker or conical flask, and stir the solution at a rate of 250±50 r.min−1 for 16 hours (instead of for 1 hour, as is set out in EDANA test method NWSP 270.0.R2 (15)).

9.8 Prepare a titration blank by treating 200.0±0.1 ml of the same batch of saline solution as used for the sample preparation in the same way. Deviation from EDANA test method NWSP 270.0.R2 (15): n=2.

9.9 Stop stirring the solutions, and filter the extracted sample directly with a screen-covered beaker (CCRC beaker) with no downtime (instead of allowing the gel to completely settle to the bottom of the beaker, as is set out in EDANA test method NWSP 270.0.R2 (15)).

Calculation of Average Distance Rxl Between Neighboring Crosslinks and an Average Diameter of Gyration 2*Rg SAP material is synthesized via polymerization of acrylic acid with internal crosslinker comonomers that possess at least two reactive polymerizable groups (the number of polymerizable groups per crosslinker comonomer is often dubbed functionality and denoted with f). The obtained network polymer has an average crosslink density depending on the add-on level of said crosslinker monomer (denoted as CXL %, in % mol vs. acrylic acid monomer % mol). The copolymerization reaction is a random radical reaction wherein the average crosslink distribution in the polymer can be calculated in terms of average number of acrylic acid (AA) monomer units (including also sodium acrylate units as acrylic acid may be neutralized in situ to a certain degree) between crosslinking monomers. As it can be assumed that the majority of crosslinker monomers have reacted all their available polymerizable groups, the average number of AA units between two neighboring crosslinking molecules would be $N_{xl}$ (see equation 1). Therefore:

$$N_{xl} = \frac{100}{f \cdot CXL_\%} \tag{1}$$

It can be recognized that during synthesis, the chains grow and crosslink randomly in stress-free state (no external force field) and therefore the chain dimensions obey a random conformation which could at first approximation be described by Flory's equation relating the average end-to-end geometrical distance in space ($R_{ee}$) of a self-avoiding polymer chain (i.e. accounting for excluded volume of the chain but in this case neglecting concentration and ionic interactions factors because all considered gel have similar polymer solid content and ionic charge) to the number (N) and individual size of monomer units (b) that build it (see also P. J. Flory, Principles of Polymer Chemistry, Cornell University Press, Ithaca (1953)):

$$R_{ee} = b \cdot N^{3/5} \tag{2}$$

For the situation of a random infinitely large network described above, the $R_{ee}$ value for a solution synthesis in stress-free conditions (native conditions) of a network, could be used to evaluate the distance between two adjacent crosslinks, denoted by $R_{xl}(n)$ for native state. Therefore, $R_{xl}(n)$ would be dependent on the number of AA units in-between these crosslinks ($N_{xl}$) and the size of monomer units b (for acrylic acid AA b≈2.7 Å=0.27 nm):

$$R_{xl}(n) = b \cdot N_{xl}^{3/5} \tag{3}$$

Substituting (1) into (3), therefore leads to:

$$R_{xl}(n) = b \cdot \left(\frac{100}{f \cdot CXL_\%}\right)^{3/5} \tag{4}$$

As is characteristic for SAP material, after preparation, the polymer can be subjected to swelling with a liquid (e.g. urine, saline or pure water) which leads to large volumetric expansion of the network to an equilibrium capacity, e.g. measured by centrifuge retention capacity (CRC). During swelling therefore, the $R_{xl}$ distance between two adjacent crosslinks will increase accordingly to accommodate for the volumetric expansion of the network. At certain level of swelling, whether equilibrium or not (denoted as x-load, xL in grams of liquid per gram of dry SAP material), the crosslink-to-crosslink distance goes from $R_{xl}(n)$ to $R_{xl}(xL)$. Most typically, modern SAP materials used in absorbent articles swell at equilibrium (CRC) to about 30 g of urine (or saline with 0.9% w NaCl) per gram of dry SAP material (if their capacity (CRC) is less than 30 g/g, they of course absorb less than 30 g/g). On average, in diapers or pants use, SAP material is swollen to about 20 g/g before the caretaker changes the diaper or pant (i.e. diaper change is typically done before the maximum possible amount of urine has been absorbed by the SAP material), or—during night or other prolonged use- to about 25 g/g. Therefore, for the present invention, the ratio claimed herein refers to a load of the SAP material of 20 g/g, i.e. $R_{xl}$ is calculated for a load of 20 g/g. In addition, $R_{xl}$ for a load of 25 g/g is also provided for the examples herein below. As x-load is defined as mass of liquid per dry mass of SAP material, to calculate the volumetric expansion of the network (proportional to the increase in $R_{xl}$ raised to the cube power for isotropic swelling) at a given x-load (xL), one would need the density of the dry SAP material ($r_d$) and the density of the swelling liquid ($r_{liq}$).

Figure 7:
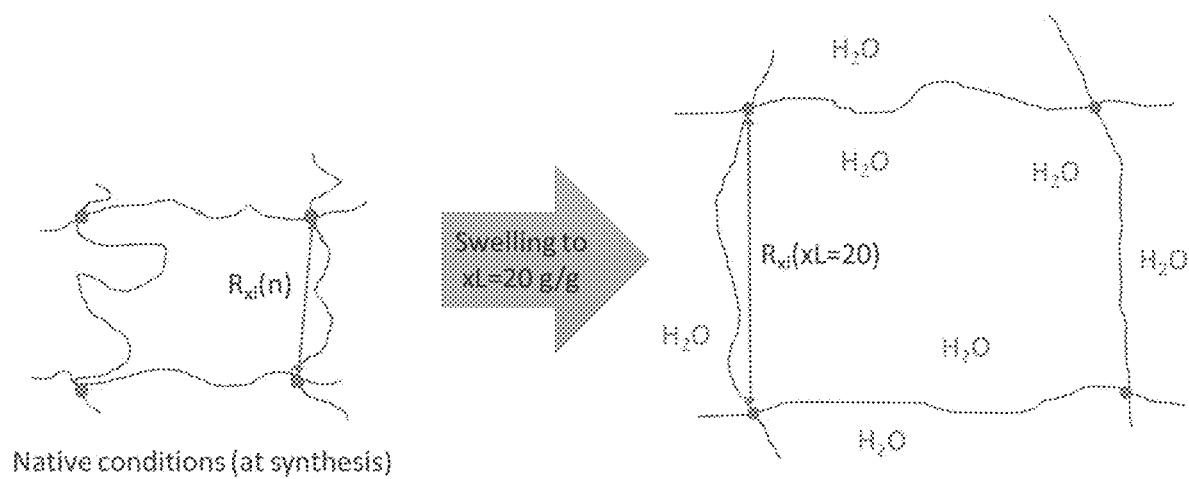
FIG. 7 is a schematic of network structure at native state and after swelling with fluid.

Scheme 1. Schematic illustration of network structure at native state and after swelling with fluid is illustrated in FIG. 7.

Calculation of $R_{xl}(xL)$

First it is assumed that swelling from native to any other xL different from the native (denoted by index (n)), is isotropic, i.e. homogeneous and equal in all directions, therefore the volume ratio at given xL to native equals the ratio of the cubes of the crosslink-to-crosslink distances $R_{xl}$ at given xL to native one:

$$\left(\frac{R_{xl}(xL)}{R_{xl}(n)}\right)^3 = \frac{V_{(xL)}}{V_{(n)}} \tag{5}$$

Recognizing that the volumes upon swelling from native to given xL are additive (i.e. no dilation or contraction):

$$V_{(xL)} = V_{(n)} + V_{liq} \tag{6}$$

and by definition xL is defined as the mass of swelling liquid $m_{liq}$ per mass of dry SAP material ($m_d$):

$$xL = \frac{m_{liq}}{m_d} \tag{7}$$

and the volume of the swelling liquid is simply the ratio of $m_{liq}$ to its resp. density ($r_{liq}$):

$$V_{liq} = \frac{m_{liq}}{\rho_{liq}} \tag{8}$$

the volume of the swelling liquid $V_{liq}$ can be expressed by substituting (7) into (8) and then into (6) and finally into (5) to obtain:

$$\left(\frac{R_{xl}(xL)}{R_{xl}(n)}\right)^3 = \frac{V_{(n)} + \frac{xL \cdot m_d}{\rho_{liq}}}{V_{(n)}} = 1 + \frac{xL \cdot m_d}{\rho_{liq} V_{(n)}} \tag{9}$$

Next, the native volume of the SAP $V_{(n)}$ can be expressed, assuming colligative properties of the volume when synthesizing SAP in aqueous solution, where $V_d$ is the dry SAP material volume and $V_w$ is the volume of water from the polymerization solution which remains in the native SAP material:

$$V_{(n)} = V_d + V_w \tag{10}$$

wherein substitution of volumes with the resp. mass to density ratios (by definition) of the dry polymer ($m_d$ and $r_d$) and water ($m_w$ and $r_w$) leads to:

$$V_{(n)} = \frac{m_d}{\rho_d} + \frac{m_w}{\rho_w} \quad (11)$$

An important parameter when synthesizing SAP material is the solid content at synthesis which is the amount of dry SAP material related to the overall weight of the native SAP material (wherein the sum of dry polymer and water is the native gel weight). By definition, solid content in the native conditions w can be expressed as:

$$\omega = \frac{m_d}{m_{(n)}} = \frac{m_d}{m_d + m_w} = \frac{1}{1 + \frac{m_w}{m_d}} \quad (12)$$

From this the $m_w$ in native gel can therefore be expressed as:

$$m_w = m_d \cdot \left(\frac{1}{\omega} - 1\right) \quad (13)$$

Substituting (13) into (11) and recognizing $r_w = 1$ g/ccm leads to:

$$V_{(n)} = \frac{m_d}{\rho_d} + \frac{m_d \cdot \left(\frac{1}{\omega} - 1\right)}{\rho_w} = m_d \cdot \left(\frac{1}{\rho_d} + \frac{1}{\omega} - 1\right) \quad (14)$$

Substituting (14) into (9) and simplifying then leads to:

$$\left(\frac{R_{xl}(xL)}{R_{xl}(n)}\right)^3 = 1 + \frac{xL}{\rho_{liq} \cdot \left(\frac{1}{\rho_d} + \frac{1}{\omega} - 1\right)} \quad (15)$$

Therefore, the $R_{xl}(xL)$ can be expressed as the native $R_{xl}(n)$ (obtainable from (4)), multiplied by the cube root of the volumetric expansion factor (function of xL, densities of dry SAP material and swelling liquid and solid content of native gel w):

$$R_{xl}(xL) = R_{xl}(n) \cdot \left[1 + \frac{xL}{\rho_{liq} \cdot \left(\frac{1}{\rho_d} + \frac{1}{\omega} - 1\right)}\right]^{1/3} \quad (16)$$

$$= b \cdot \left(\frac{100}{f \cdot CXL_\%}\right)^{3/5} \cdot \left[1 + \frac{xL}{\rho_{liq} \cdot \left(\frac{1}{\rho_d} + \frac{1}{\omega} - 1\right)}\right]^{1/3}$$

For the most common type of SAP used in diapers to swell with urine, based on AA monomer and internally crosslinked via bifunctional crosslinkers like PEG-diacrylate (PEGDA), the following constants are in place (approximately):

| Parameter | Value |
| --- | --- |
| b | 0.27 nm |
| f | 2 |
| $\rho_d$ | 1.6 g/cm$^3$ |
| $\rho_{liq}$ | 1.004 g/cm$^3$ |

If the SAP material comprises comonomers, the value of b has to be adjusted accordingly. For mixtures of monomers and co-monomers, a weighted average value of b has to be calculated based on the individual sizes of the different monomers and their proportion in the monomer/co-monomer mixture. The same applies if mixtures or combinations of different crosslinker molecules are applied with regard to calculation of the number of polymerizable groups per crosslinker comonomer f.

For calculation of $R_{xl}$ herein, possible surface cross-linking of SAP particles is not taken into consideration. Surface cross-linking only impacts a neglectable mass proportion of the cross-linked polyacrylic acid network of the SAP particle as only a very thin area on the surface is subjected to additional cross-linking. Moreover, for the present invention, $R_{xl}$ values for SAP particle loads of 20 g/g are calculated. At such load, the SAP particle has undergone considerable expansion and swelling which leads to significant breaks in the surface-crosslinks. Hence, the Rxl values calculated for the base polymer particles as provided herein are equally applicable to SAP particles that have been subjected to surface cross-linking.

As s-PAA polymers are incorporated during SAP material synthesis, the chains of the s-PAA polymers are not reactive during the polymerization of AA monomer (apart from a rare chain transfer to a radical). So as the SAP material network forms around these s-PAA polymer chains, it may be that the latter are considerably larger than the network pores between crosslinks, due to the high solid content at synthesis (native condition). This leads to significant interpenetration of s-PAA polymer chains into the network and therefore entanglement between the s-PAA polymer chains from the free polymer and from the network. When swelling in large amounts of liquid occurs, e.g. 20 g/g or higher, the volumetric dilation of the network leads to significant increase and stretching of the polyacrylic acid chains comprising by and polymerized into the network. The dilution effect helps the free s-PAA polymer chains to take a more relaxed conformation from entangled semi-dilute or concentrated regime to dilute regime. As these free s-PAA polymer chains form less entangled or even unentangled chain conformations in dilute regime with a characteristic size described by their radius of gyration $R_g$ proportional to their molecular weight (see eq. (17)), their molecules can move within the network depending on their size and on the size of the network pores. When the size of the free s-PAA polymer chains is relatively bigger than the pores of the network, it will be more difficult for the said free s-PAA polymer chains to migrate within the network and especially to reach the surface of a SAP particle in excess swelling liquid and depart from it, becoming therefore extractable polymer. When the mobile s-PAA polymer chains have smaller $R_g$ and size than the network pore (as shown on Scheme 2), they are able to move more freely within the gel network pores and eventually depart through the surface of the SAP particles as extractable polymer. As said above, absorbent articles, such as diapers and pants, are often changed well before the SAP particles reach their maximum capacity, i.e. the SAP particles have only been loaded to about 20 g/g. Therefore, for the present invention, we focus on $R_{xl}$ values for a load of 20 g/g when calculating the ratio of $2*R_g/R_{xl}$, to ensure that the s-PAA polymers that are comprised by the SAP particles of the present invention are readily prevented from migration at SAP particles loads as are typical in in-use conditions of absorbent articles.

Figure 8:
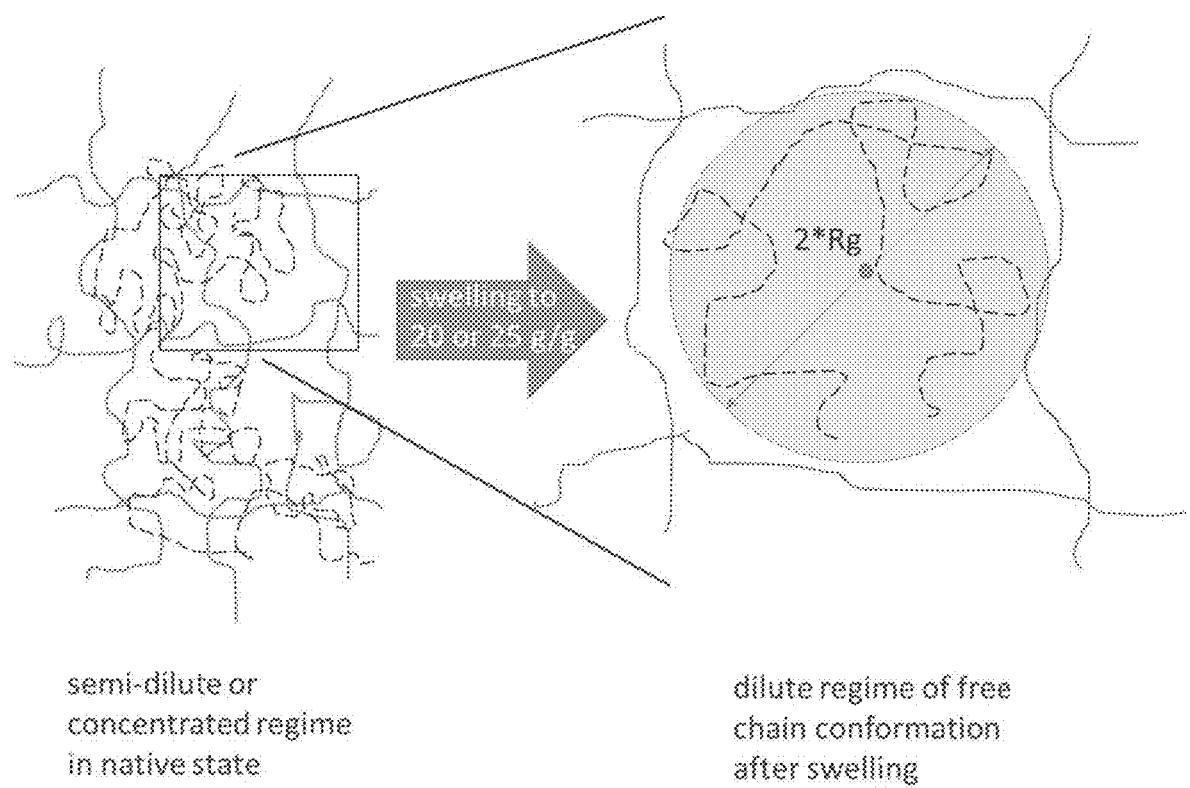
FIG. 8 is a schematic of incorporated non-crosslinked polymer into SAP polymer.

Scheme 2. Incorporated non-crosslinked s-PAA polymer into SAP polymer is illustrated in FIG. 8. Note the chemistries of the incorporated polymer and the network are the same (e.g. typically partially neutralized polyacrylic acid based) and are herein shown in different color to denote their different connectivity.

Interrupted lines in Scheme 2, as shown in FIG. 8, illustrate polymer chains. The interrupted line is not intended to show breaks in the chain but meant to ease distinction between lines showing cross-linked polymer network and lines show in sPAA polymers As mentioned above, the conformation and chain dimensions of the s-PAA polymers may be expressed via their radius of gyration. The sphere with the same radius would therefore approximate the folded chain and the former would therefore have a size of 2*Rg (diameter). The radius of gyration can be approximated conveniently for free chains including the excluded volume via the relation obtained from the renormalization group theory (J. des Cloizeaux, G. Jannink, Polymers in Solution: Their Modelling and Structure, Oxford Univ. Press: Clarendon (1990)) and (2):

$$R_g = \frac{\sqrt{0.952} \cdot b \cdot N^{3/5}}{\sqrt{6}} \approx 0.40 \cdot b \cdot N^{3/5} \tag{17}$$

The value N here is the average number of monomer units (in this case partially neutralized acrylic acid). It can be calculated from the weight average molecular weight $M_w$ of the polymer chains and the average molecular weight of the partially neutralized acrylic acid monomer, wherein the degree of neutralization of the acrylic acid is 68% mol and therefore $M_m \approx 87$ g/mol:

$$N = \frac{M_w}{M_m} \tag{18}$$

Substituting (18) into (17) gives a convenient way to estimate the $R_g$ of the incorporated s-PAA polymers:

$$R_g = 0.40 \cdot b \cdot \left(\frac{M_w}{M_m}\right)^{3/5} \tag{19}$$

wherein the degree of neutralization of the acrylic acid at 68% mol producing average monomer molecular weight of $M_m \approx 87$ g/mol and the value for b is approximately 0.27 nm. The values of $R_g$ for all incorporated s-PAA polymers therefore can be easily calculated and compared to the $R_{xl}$ distances at xL=20 g/g, etc.

The average, or effective, molecular weight of a monomer of the partially neutralized acrylic acid based SAP material can be calculated from the mol. weight of the acrylic acid monomer. The soluble PAA polymers will have the same degree of neutralization as the rest of the SAP material as counterions like $Na^{30}$ are mobile. The effective mol. weight of the monomer of the s-PAA polymer at a given degree of neutralization (DN, % mol) will be the mole weighted average of the mol. weights of the pure acrylic acid monomer ($M_{AA}$=72.06 g/mol) and the sodium acrylate monomer ($M_{NaAA}$=94.04 g/mol) (see eq. 20). Therefore, at DN=68% mol, the effective monomer mol. weight would be 87.02 g/mol≈87 g/mol Equation 20. Determination of effective mol. weight of PAA monomer MWm unit at specific DN % mol:

$$MW_m = DN_\% \cdot MW_{NaAA} + (100 - DN_\%) \cdot MW_{AA} \tag{20}$$

Extractable polymer in SAP material is a major challenge in SAP material technology as the former represents polymer which is mobile and not part of the network. As it comprises the same charged partially neutralized polyacrylic acid chemistry, the extractable polymer contributes to capacity via osmotic pressure only if it is within the SAP network structure. Once it leaves the network respectively the SAP particles during swelling, extractable polymer has negative impact on capacity. This happens on two accounts. Firstly, by migrating out of the SAP particles, the extractable polymer decreases the active mass of swellable polymer. Secondly, the extractable polymer by being also charged polymer, increases the osmotic pressure outside the SAP particles, which decreases further the capacity thereof. Especially negative impact is found for absorption against pressure (AAP) which is even more sensitive to osmotic pressure gradient outside and inside SAP particles. At the same time, inherently, extractable polymer as not being connected to the network, does not contribute to mechanical strength of the SAP material network. Therefore, extractable polymer impacts negatively both capacity and mechanical strength (related to flow permeability (SFC/UPM)) of the SAP material. As is well known in the art, these two performance parameters are inversely related, and hence extractable polymer is undesired in SAP material Generally, the amount of extractable polymer in commercially relevant SAP materials varies between 4 and 15% w for surface-crosslinked materials and 8-17% w for base polymer SAPs. As extractable polymer is inversely related to capacity in a tradeoff relationship, it is to be expected that SAP materials with higher capacity will exhibit higher extractables and vice versa.

EXAMPLES

Various examples of the present invention as well as comparative examples have been prepared and evaluated.

The inventive examples differ a) in the weight average molecular weight. $M_w$ of the s-PAA polymers, b) in the amount of s-PAA polymers comprised by the SAP particles, and c) in the source of the s-PAA polymers (different commercially available s-PAA polymers as dwell as s-PAA polymers obtained from different SAP particle degradation methods).

Among the comparative examples are SAP materials where no s-PAA polymers have been added during making of the SAP material, as well as examples using s-PAA polymers of relatively low mass average molecular weight $M_w$. The examples with low mass average molecular weight $M_w$ have a ratio of $2*R_g$ to $R_{xl}$ of below 1.0.

TABLE 1

Overview I of Examples A1 to A7 and Comparative Examples C1 to C8

| Example | Base Polymer | s-PAA polymer | Mw s-PAA polymer, kDa | CXL Mol ratio vs AA monomer | s-PAA polymer add-on level, % w | solid content "w" at synthesis, % wt |
|---|---|---|---|---|---|---|
| A1 | BP A1 | Sigma-Aldrich | 720 | 0.075 | 10 | 27.9 |
| A2 | BP A2 | Sigma-Aldrich | 720 | 0.075 | 5 | 28.0 |
| A3 | BP A3 | PAA A3 | 525 | 0.075 | 10 | 27.0 |
| A4 | BP A4 | PAA A4 | 1080 | 0.075 | 5 | 28.0 |
| A5 | BP A5 | PAA A5 | 418 | 0.075 | 5 | 28.0 |
| A6 | BP A6 | Sigma-Aldrich | 1000 *) | 0.075 | 4 | 27.9 |
| A7 | BP A7 | Sigma-Aldrich | 720 | 0.075 | 20 | 28.0 |
| C1 | BP C1 | None | none | 0.075 | 0 | 28.0 |
| C2 | BP C1 | None | none | 0.075 | 0 | 28.0 |
| C3 | BP C3 | none | none | 0.18 | 0 | 28.2 |
| C4 | BP C4 | Sokalan PA 110 S (BASF) | 223 | 0.086 | 10 | 28.0 |
| C5 | BP C5 | Sokalan PA 110 S (BASF) | 223 | 0.075 | 10 | 31.8 |
| C6 | BP C6 | Sigma-Aldrich | 100 *) | 0.075 | 10 | 27.9 |
| C7 | BP C7 | Sokalan PA 110 S (BASF) | 223 | 0.075 | 5 | 28.0 |
| C8 | BP C8 | Sigma-Aldrich | 100 *) | 0.075 | 5 | 27.9 |

*) the molecular weight of the s-PAA polymer of example A6, and comparative example C6 and C8 was not determined by the test method set out herein. Instead, the molecular weight was given on the label of the commercial s-PAA polymer was taken.

TABLE 2

Overview II of Examples A1 to A7 and Comparative Examples C1 to C8

| EXAMPLE | Avg native XL-XL monomers $N_{xl}$ (n) | $R_{xl}$ (n), nm | $R_{xl}$ (xL = 20)[1], nm | $R_{xl}$ (xL = 25)[2], nm | $2 * R_g$ of s-PAA polymer, nm | Ratio $2R_g/R_{x1}$[1] (@20 g/g) | Ratio $2R_g/R_{x1}$[2] (@25 g/g) |
|---|---|---|---|---|---|---|---|
| A1 | 667 | 13.4 | 25.9 | 27.6 | 48.4 | 1.87 | 1.75 |
| A2 | 667 | 13.4 | 25.9 | 27.6 | 48.4 | 1.87 | 1.75 |
| A3 | 667 | 13.4 | 25.6 | 27.3 | 40.1 | 1.56 | 1.47 |
| A4 | 667 | 13.4 | 25.9 | 27.6 | 61.8 | 2.39 | 2.24 |
| A5 | 667 | 13.4 | 25.9 | 27.6 | 35.0 | 1.35 | 1.27 |
| A6 | 667 | 13.4 | 25.9 | 27.6 | 59.0 | 2.28 | 2.14 |
| A7 | 667 | 13.4 | 25.9 | 27.6 | 48.4 | 1.87 | 1.75 |
| C1 | 667 | 13.4 | 25.9 | 27.6 | — | — | — |
| C2 | 667 | 13.4 | 25.9 | 27.6 | — | — | — |
| C3 | 278 | 7.9 | 15.4 | 16.4 | — | — | — |
| C4 | 581 | 12.3 | 23.8 | 25.5 | 24.0 | 1.01 | 0.94 |
| C5 | 667 | 13.4 | 27.0 | 28.9 | 24.0 | 0.89 | 0.83 |
| C6 | 667 | 13.4 | 25.9 | 27.6 | 14.8 | 0.57 | 0.54 |
| C7 | 667 | 13.4 | 25.9 | 27.6 | 24.0 | 0.93 | 0.87 |
| C8 | 667 | 13.4 | 25.9 | 27.6 | 14.8 | 0.57 | 0.54 |

[1] Calculated for SAP particles being loaded with 20 g of saline with 0.9% w NaCl, per gram of dry SAP material.
[2] Calculated for SAP particles being loaded with 25 g of saline with 0.9% w NaCl, per gram of dry SAP material.

Preparation of Base Polymer BP C1 of Comparative Examples C1 and C2:

A 20,000 ml resin kettle (equipped with a four-necked glass cover closed with septa, suited for the introduction of a thermometer, syringe needles) was charged with about 5097.0 g of ice (ca. 50% of the total amount of ice: 9676.1 g ice prepared from deionized water). A magnetic stirrer, capable of mixing the whole content (when liquid), was added and stirring was started.

About 200.0 g of deionized water was taken to dissolve 5.181 g of "KPS" (=potassium peroxydisulfate, from Sigma Aldrich) e.g. in a glass beaker of 250 mL volume. The vessel with the "KPS" solution was closed and set aside.

About 10.0 g of deionized water was taken to dissolve 0.112 g of "ASC" (=Ascorbic Acid, from Sigma Aldrich) e.g. in a glass vial of 40 mL volume. The vessel with the "ASC" solution was closed with a plastic snap-on cap and set aside.

200.0 g of deionized water was taken to dissolve 33.589 g of "PEG700-DA" (=polyethylene glycol diacrylate of Mn~700 Da from Sigma Aldrich) e.g. in a glass beaker. The beaker with the "PEG700-DA" solution was covered e.g. with parafilm and set aside.

The full amount of 4600.3 g of glacial AA (=acrylic acid) was added to the ice in the resin kettle while stirring was continued.

A thermometer was introduced and in total 3472.6 g of 50% w NaOH (sodium hydroxide) solution (for analysis, from Merck KGaA) and the remaining amount of ice (prepared from de-ionized water) were added subsequently in portions such that the temperature was below 30° C.

The "PEG700-DA" solution was added to the mixture of AA, NaOH solution and ice at a temperature below 30° C. while stirring was continued. The beaker that contained the "PEG700-DA" solution was washed 2× with deionized water in an amount of about 10% of the "PEG700-DA" solution volume per wash. The wash water of both washing steps was added to the stirred mixture.

Deionized water (the remaining amount required to achieve the total amount of (ice+water) of 11888.3 g was added to the stirred mixture.

Then, the resin kettle was closed, and a pressure relief was provided e.g. by puncturing two syringe needles through the septa. The solution was then purged vigorously with argon via an 80 cm injection needle at about 0.4 bar while stirring at about 400-600 RPM. The argon stream was placed close to the stirrer for efficient and fast removal of dissolved oxygen.

After about 1 hour of Argon purging and stirring, the "ASC" solution was added to the reaction mixture at a temperature of about 20° C. via plastic funnel inserted temporarily in one of the resin kettle cover necks while stirring and Argon purging was continued. Thereafter, about 0.022 g of 1% w aqueous solution of hydrogen peroxide $H_2O_2$ (Sigma-Aldrich) was added via 1 mL plastic pipette to the "KPS" solution, and the latter was then also added to the reaction mixture via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Within 5 min of "KPS" solution addition, the solution characteristically starts to become turbid or a sudden increase in viscosity was observed. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was ground with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 10 min) to the following particle size cuts with the following yields:

|  | fines | Collected fraction | crude |
|---|---|---|---|
| sieved fractions yield | <150 μm | 150-710 μm 4500 g | >710 μm |

The fractions "fines" and "crude" have been discarded and not used further.

Preparation of Base Polymer BP C3 of Comparative Example C3

A 20,000 ml resin kettle (equipped with a four-necked glass cover closed with septa, suited for the introduction of a thermometer, syringe needles) was charged with about 4528.9 g of ice (ca. 50% of the total amount of ice: 8941.1 g ice prepared from deionized water). A magnetic stirrer, capable of mixing the whole content (when liquid), was added and stirring was started.

About 200.0 g of deionized water was taken to dissolve 5.177 g of "KPS" (=potassium peroxydisulfate, from Sigma Aldrich) e.g. in a glass beaker of 250 mL volume. The vessel with the "KPS" solution was closed and set aside.

About 10.0 g of deionized water was taken to dissolve 1.124 g of "ASC" (=Ascorbic Acid, from Sigma Aldrich) e.g. in a glass vial of 40 mL volume. The vessel with the "ASC" solution was closed with a plastic snap-on cap and set aside.

200.0 g of deionized water was taken to dissolve 80.44 g of "PEG700-DA" (=polyethylene glycol diacrylate of Mn~700 Da from Sigma Aldrich) e.g. in a glass beaker. The beaker with the "PEG700-DA" solution was covered e.g. with parafilm and set aside.

The full amount of 4600.0 g of glacial AA (=acrylic acid) was added to the ice in the resin kettle while stirring was continued.

A thermometer was introduced and in total 3472.7 g of 50% w NaOH (sodium hydroxide) solution (for analysis, from Merck KGaA) and the remaining amount of ice (prepared from de-ionized water) were added subsequently in portions such that the temperature is below 30° C.

The "PEG700-DA" solution was added to the mixture of AA, NaOH solution and ice at a temperature below 30° C. while stirring is continued. The beaker that contained the "PEG700-DA" solution was washed 2× with deionized water in an amount of about 10% of the "PEG700-DA" solution volume per wash. The wash water of both washing steps was added to the stirred mixture.

The remaining amount of deionized water required to achieve the total amount of (ice+water) of 11838.6 g was added to the stirred mixture.

Then, the resin kettle was closed, and a pressure relief was provided e.g. by puncturing two syringe needles through the septa. The solution was then purged vigorously with argon via an 80 cm injection needle at about 0.4 bar while stirring at about 400. The argon stream was placed close to the stirrer for efficient and fast removal of dissolved oxygen.

After about 1 hour of Argon purging and stirring, the "ASC" solution was added to the reaction mixture at a temperature of about 20° C. via plastic funnel inserted temporarily in one of the resin kettle cover necks while stirring and Argon purging was continued. Thereafter, about 0.25 g of 1% w aqueous solution of hydrogen peroxide $H_2O_2$ (Sigma-Aldrich) was added via 1 mL plastic pipette to the "KPS" solution, and the latter was then also added to the reaction mixture via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 2 min of "KPS" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~4200 g | >710 μm |

The fractions "fines" and "crude" have been discarded and not used further.

Preparation of Base Polymer BP C4 of Comparative Example C4

A 10,000 ml resin kettle (equipped with a four-necked glass cover closed with septa, suited for the introduction of a thermometer, syringe needles) was charged with about 2258.0 g of ice (ca. 60% of the total amount of ice: 3882.7 g ice prepared from deionized water). A magnetic stirrer, capable of mixing the whole content (when liquid), was added and stirring was started.

About 100.0 g of deionized water was taken to dissolve 2.276 g of "KPS" (=potassium peroxydisulfate, from Sigma Aldrich) e.g. in a glass beaker of 250 mL volume. The vessel with the "KPS" solution was closed and set aside.

About 10.0 g of deionized water was taken to dissolve 0.493 g of "ASC" (=Ascorbic Acid, from Sigma Aldrich) e.g. in a glass vial of 40 mL volume. The vessel with the "ASC" solution was closed with a plastic snap-on cap and set aside.

200.0 g of deionized water was taken to dissolve 16.78 g of "PEG700-DA" (=polyethylene glycol diacrylate of Mn~700 Da from Sigma Aldrich) e.g. in a glass beaker. The beaker with the "PEG700-DA" solution was covered e.g. with parafilm and set aside.

The full amount of 2020.6 g of glacial AA (=acrylic acid) was added to the ice in the resin kettle while stirring was continued.

An amount of 799.2 g of Sokalan® PA 110 S (BASF) comprising aqueous polyacrylic acid solution of about 35% w concentration wherein the weight average molecular weight Mw, determined by Gel Permeation Chromatography reported by size exclusion chromatography was 223 kDa (test method as described herein above), was added to the mixture in the resin kettle while stirring was continued.

A thermometer was introduced and in total 1736.3 g of 50% w NaOH (sodium hydroxide) solution (for analysis, from Merck KGaA) and the remaining amount of ice (prepared from de-ionized water) were added subsequently in portions such that the temperature was below 30° C.

The "PEG700-DA" solution was added to the mixture of AA, NaOH solution and ice at a temperature below 30° C. while stirring was continued. The beaker that contained the "PEG700-DA" solution was washed 2× with deionized water in an amount of about 10% of the "PEG700-DA" solution volume per wash. The wash water of both washing steps was added to the stirred mixture.

Deionized water (the remaining amount required to achieve the total amount of (ice+water) of 5422.6 g was added to the stirred mixture.

Then, the resin kettle was closed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, the "ASC" solution was added to the reaction mixture at a temperature of about 20° C. via plastic funnel inserted temporarily in one of the resin kettle cover necks while stirring and Argon purging was continued. Thereafter, about 1.00 g of 1% w aqueous solution of hydrogen peroxide $H_2O_2$ (Sigma-Aldrich) was added via 1 mL plastic pipette to the "KPS" solution, and the latter was then also added to the reaction mixture via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 2 min of "KPS" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~2100 g | >710 μm |

The fractions "fines" and "crude" have been discarded and not used further.

Preparation of Base Polymer BP C5 of Comparative Example C5

A 10,000 ml resin kettle (equipped with a four-necked glass cover closed with septa, suited for the introduction of a thermometer, syringe needles) was charged with about 2536.1 g of ice (ca. 60% of the total amount of ice: 3050.3 g ice prepared from deionized water). A magnetic stirrer, capable of mixing the whole content (when liquid), was added and stirring was started.

About 100.0 g of deionized water was taken to dissolve 2.599 g of "KPS" (=potassium peroxydisulfate, from Sigma Aldrich) e.g. in a glass beaker of 250 mL volume. The vessel with the "KPS" solution was closed and set aside.

About 10.0 g of deionized water was taken to dissolve 0.566 g of "ASC" (=Ascorbic Acid, from Sigma Aldrich) e.g. in a glass vial of 40 mL volume. The vessel with the "ASC" solution was closed with a plastic snap-on cap and set aside.

200.0 g of deionized water was taken to dissolve 16.76 g of "PEG700-DA" (=polyethylene glycol diacrylate of Mn~700 Da from Sigma Aldrich) e.g. in a glass beaker. The beaker with the "PEG700-DA" solution was covered e.g. with parafilm and set aside.

The full amount of 2300.1 g of glacial AA (=acrylic acid) was added to the ice in the resin kettle while stirring was continued.

An amount of 908.7 g of Sokalan® PA 110 S (BASF) comprising aqueous polyacrylic acid solution of about 35% w concentration wherein the weight average molecular weight Mw determined by Gel Permeation Chromatography reported by size exclusion chromatography was 223 kDa (test method as described herein above), was added to the mixture in the resin kettle while stirring was continued.

A thermometer was introduced and in total 1975.4 g of 50% w NaOH (sodium hydroxide) solution (for analysis, from Merck KGaA) and the remaining amount of ice (prepared from de-ionized water) were added subsequently in portions such that the temperature was below 30° C.

The "PEG700-DA" solution was added to the mixture of AA, NaOH solution and ice at a temperature below 30° C. while stirring was continued. The beaker that contained the "PEG700-DA" solution was washed 2× with deionized water in an amount of about 10% of the "PEG700-DA" solution volume per wash. The wash water of both washing steps was added to the stirred mixture.

Deionized water (the remaining amount required to achieve the total amount of (ice+water) of 4795.0 g was added to the stirred mixture.

Then, the resin kettle was closed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, the "ASC" solution was added to the reaction mixture at a temperature of about 20° C. via plastic funnel inserted temporarily in one of the resin kettle cover necks while stirring and Argon purging was continued. Thereafter, about 1.90 g of 1% w aqueous solution of hydrogen peroxide $H_2O_2$ (Sigma-Aldrich) was added via 1 mL plastic pipette to the "KPS" solution, and the latter was then also added to the reaction mixture via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 2 min of "KPS" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~2100 g | >710 μm |

The fractions "fines" and "crude" have been discarded and not used further.

Preparation of Base Polymer BP C6 of Comparative Example C6

A 10,000 ml resin kettle (equipped with a four-necked glass cover closed with septa, suited for the introduction of a thermometer, syringe needles) was charged with about 2392.1 g of ice (ca. 60% of the total amount of ice: 3622.5 g ice prepared from deionized water). A magnetic stirrer, capable of mixing the whole content (when liquid), was added and stirring was started.

About 100.0 g of deionized water was taken to dissolve 2.296 g of "KPS" (=potassium peroxydisulfate, from Sigma Aldrich) e.g. in a glass beaker of 250 mL volume. The vessel with the "KPS" solution was closed and set aside.

About 10.0 g of deionized water was taken to dissolve 0.492 g of "ASC" (=Ascorbic Acid, from Sigma Aldrich) e.g. in a glass vial of 40 mL volume. The vessel with the "ASC" solution was closed with a plastic snap-on cap and set aside.

200.0 g of deionized water was taken to dissolve 14.71 g of "PEG700-DA" (=polyethylene glycol diacrylate of Mn~700 Da from Sigma Aldrich) e.g. in a glass beaker. The beaker with the "PEG700-DA" solution was covered e.g. with parafilm and set aside.

The full amount of 2020.3 g of glacial AA (=acrylic acid) was added to the ice in the resin kettle while stirring was continued.

An amount of 798.5 g of solution (Sigma Aldrich) comprising aqueous polyacrylic acid of about 35% w concentration wherein the weight average molecular weight Mw as reported by the supplier Sigma Aldrich is 100,000 Da, was added to the mixture in the resin kettle while stirring was continued.

A thermometer was introduced and in total 1735.5 g of 50% w NaOH (sodium hydroxide) solution (for analysis, from Merck KGaA) and the remaining amount of ice (prepared from de-ionized water) were added subsequently in portions such that the temperature was below 30° C.

The "PEG700-DA" solution was added to the mixture of AA, NaOH solution and ice at a temperature below 30° C. while stirring was continued. The beaker that contained the "PEG700-DA" solution was washed 2× with deionized water in an amount of about 10% of the "PEG700-DA" solution volume per wash. The wash water of both washing steps was added to the stirred mixture.

Deionized water (the remaining amount required to achieve the total amount of (ice+water) of 5429.5 g was added to the stirred mixture.

Then, the resin kettle was closed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, the "ASC" solution was added to the reaction mixture at a temperature of about 20° C. via plastic funnel inserted temporarily in one of the resin kettle cover necks while stirring and Argon purging was continued. Thereafter, about 0.99 g of 1% w aqueous solution of hydrogen peroxide $H_2O_2$ (Sigma-Aldrich) was added via 1 mL plastic pipette to the "KPS" solution, and the latter was then also added to the reaction mixture via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 2 min of "KPS" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~2100 g | >710 μm |

The fractions "fines" and "crude" have been discarded and not used further.

Preparation of Base Polymer BP C7 of Comparative Example C7

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 80.0 g of solution comprising aqueous polyacrylic acid (PAA) of about 35% w concentration wherein the weight average molecular weight Mw determined by Gel Permeation Chromatography reported by size exclusion chromatography was 223 kDa (test method as described herein above). About 496.6 g water was added as ice prepared from DI water and DI water of weight about 497.5 g was also added to the mixture. A magnetic stirrer, capable of mixing the whole content, was added and stirring was started.

As the PAA was fully dispersed, the full amount of 432.5 g of glacial AA (=acrylic acid) was added to the PAA solution in the resin kettle while stirring was continued.

About 13.6 g of deionized water was taken to dissolve 0.4874 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.0529 g of "ASC" (=Ascorbic Acid, from Sigma Aldrich) e.g. in a glass vial of 40 mL volume. The vessel with the "ASC" solution was closed with a plastic snap-on cap and set aside.

About 115 g of deionized water was taken to dissolve 3.15 g of "PEG700-DA" (=polyethylene glycol diacrylate of Mn~700 Da from Sigma Aldrich) e.g. in a 250 mL glass beaker. The beaker with the "PEG700-DA" solution was covered e.g. with parafilm and set aside.

The remaining 3.60 g of water up to a final weight of 1136.3 g was added to the resin kettle and stirring was continued as a homogeneous solution was obtained within 1-5 minutes.

A thermometer was introduced and in total 347.6 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about min 10 min to 1 hour of Argon purging and stirring, about 0.03 g (about 1-2 droplets) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was below about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 µm | 150-710 µm ~350 g | >710 µm |

The fractions "fines" and "crude" have been discarded and not used further.

Preparation of Base Polymer BP C8 of Comparative Example C8

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 80.0 g of solution comprising aqueous polyacrylic acid (PAA) of about 35% w concentration wherein the weight average molecular weight Mw as reported by the supplier Sigma Aldrich is 100,000 Da. About 591.4 g water was added as ice prepared from DI water and DI water of weight about 443.6 g was also added to the mixture. A magnetic stirrer, capable of mixing the whole content, was added and stirring was started.

As the PAA was fully dispersed, the full amount of 432.5 g of glacial AA (=acrylic acid) was added to the PAA solution in the resin kettle while stirring was continued.

About 20.0 g of deionized water was taken to dissolve 0.4870 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.053 g of "ASC" (=Ascorbic Acid, from Sigma Aldrich) e.g. in a glass vial of 40 mL volume. The vessel with the "ASC" solution was closed with a plastic snap-on cap and set aside.

About 70 g of deionized water was taken to dissolve 3.15 g of "PEG700-DA" (=polyethylene glycol diacrylate of Mn~700 Da from Sigma Aldrich) e.g. in a 100 mL glass beaker. The beaker with the "PEG700-DA" solution was covered e.g. with parafilm and set aside.

The remaining water up to a final weight of 1136.3 g was added to the resin kettle and stirring was continued as a homogeneous solution was obtained within 1-5 minutes.

A thermometer was introduced and in total 347.5 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, about 0.026 g (about 1-2 droplets) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was below about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710μm ~350 g | >710 μm |

The fractions "fines" and "crude" have been discarded and not used further.

Preparation of Base Polymer BP A1 of Example A1

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 1017.0 g of solution comprising aqueous polyacrylic acid (PAA) of about 5.5% w concentration wherein the viscosity average molecular weight Mv as reported by the supplier Sigma-Aldrich is 450,000 Da. The 5.5% w aqueous solution was prepared earlier as a stock solution by mixing in and stirring overnight of 110.0 g of dry PAA polymer with reported viscosity average mol. weight Mv 450,000 Da (Sigma-Aldrich) into 1890.0 g of DI water in a 3 L glass beaker. A magnetic stirrer, capable of mixing the whole content (when liquid), was added and stirring was started.

The full amount of 404.4 g of glacial AA (=acrylic acid) was added to the PAA solution in the resin kettle while stirring was continued.

About 20.0 g of deionized water was taken to dissolve 0.444 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.015 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 2.974 g of "PEG700-DA" (=polyethylene glycol diacrylate of g of Mn~700 Da from Sigma Aldrich) e.g. in a 50 mL glass beaker. The beaker with the "PEG700-DA" solution was covered e.g. with parafilm and set aside.

The remaining amount of water up to a final weight of 232.2 g was added to the resin kettle and stirring was continued as a homogeneous solution was obtained within 1-5 minutes.

A thermometer was introduced and in total 345.9 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about min 10 min to 1 hour of Argon purging and stirring, about 0.005 g (about 1 droplet) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~350 g | >710 μm |

The fractions "fines" and "crude" have been discarded and not used further.

Preparation of Base Polymer BP A2 of Example A2

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 1118.0 g of solution comprising aqueous polyacrylic acid (PAA) of about 2.5% w concentration wherein the viscosity average molecular weight Mv as reported by the supplier Sigma-Aldrich is 450,000 Da. The 2.5% w aqueous solution was prepared earlier as a stock solution by mixing in and stirring overnight of 50.0 g of dry PAA polymer with reported viscosity average mol. weight Mv 450,000 Da (Sigma Aldrich) into 1950.0 g of DI water in a 3 L glass beaker. A magnetic stirrer, capable of mixing the whole content (when liquid), was added and stirring was started.

The full amount of 431.9 g of glacial AA (=acrylic acid) was added to the PAA solution in the resin kettle while stirring was continued.

About 20.0 g of deionized water was taken to dissolve 0.487 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.011 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 3.14 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 99.1 g was added to the resin kettle and stirring was continued as a homogeneous solution was obtained within 1-5 minutes.

A thermometer was introduced and in total 347.1 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about min 10 min to 1 hour of Argon purging and stirring, about 0.017 g (about 1 droplet) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
| --- | --- | --- | --- |
| sieved fraction yield | <150 μm | 150-710 μm ~350 g | >710 μm |

The fractions "fines" and "crude" have been discarded and not used further.

Procedure to Obtain the PAA Used in Example A3 (=PAA A3) From Degradation of Pre-Existing SAP Material: Persulfate Mediated Degradation of Pre-Existing SAP Material Pre-Existing SAP Material:

The pre-existing SAP material (in the form of pre-existing SAP particles) used for degradation is commercially available in Pampers Baby Dry as marketed in Germany in 2020. The same pre-existing SAP material was used in the degradation procedure to obtain PAA A4 and PAA A5 as described below. Generally, any other commercially available acrylic acid-based pre-existing SAP material (in the form of pre-existing SAP particles) are suitable for the degradation methods described herein below.

The acrylic acid based pre-existing SAP material had a capacity (CRC) of 27.6 g/g and a moisture content of 0.4% (see UPM test method for description of how to determine moisture content). The D50 average particle size was 398 μm as measured according to ISO method 13322-2 (the Particle Size Distribution PSD was 63-710 um). The Absorption Against Pressure (AAP) of the pre-existing SAP material was 25.5 g/g, as determined by the EDANA method NWSP 242.0.R2 (15). In deviation from EDANA NWSP 242.0.R2 (15), a pressure of 0.7 psi was applied (whereas the EDANA method specifies a pressure of only 0.3 psi).

The deionized water used below was MilliporeQ. Electrical conductivity was measured with lab conductometer COND 70 INSTRUMENT without CELL, #50010522, equipped with Cell VPT51-01 C=0.1 from XS Instruments or via LF 320/Set, #300243 equipped with TetraCon® 325 from WTW, conductivity was <160 μS/cm at 0° C. Similar equipment for measuring electrical conductivity can be used accordingly.

Unless stated otherwise, the experimental procedure was performed in a climate conditioned room at standard conditions of 23° C.±2° C. temperature and 45%±10% relative humidity.

Procedure:
1. A solution of 2100 g 0.143% w potassium persulfate (KPS) was prepared by completely dissolving by stirring 3.003 g of dry KPS (Sigma-Aldrich, >=99.0% purity, inventory number 216224-500G) into 2097.0 g of deionized water placed in e.g. a 3 L glass beaker equipped with an appropriate size stir bar such that by use of magnetic stirring at about 400 rpm the full volume of solution can be well mixed. Complete dissolution of the KPS salt was observed when no visible salt crystals remain in the solution.
2. Amount of 300.0 g of dry pre-existing SAP material was measured on a balance into a glass beaker of 500 mL volume and put into the 2.5 L glass reactor for AGM synthesis (available from Normag GmbH) and the magnetic stirring was started at 500 rpm wherein subsequently 2100 g of the 0.143% w KPS stock solution was added quickly into the reactor with the pre-existing SAP material to achieve final x-load of about 7 g/g with the KPS solution. Upon swelling the viscosity of the mixture of the pre-existing SAP material and KPS solution was increasing until no more stirring was possible. The stirbar was removed from the bottom of the reactor.
3. Reactor was closed with the lid (standard lid with 4 openings). One syringe was put into the opening with gummy plug. A circulation oven (Model Binder FED720 from Binder GmbH) was preheated to 100° C. temperature. As the temperature setting was reached, the closed reactor was placed into the oven for 9 hours.
4. The reactor was taken from the oven and left to cool down below about 40° C. The obtained mixture from the reactor comprising solution and some soft swollen gel particles was filtered through a metal sieve with the mesh of 500 μm (diameter 240 mm from Retsch GmbH) placed on the top of plastic beaker with 2 L volume. Equipment was placed into the fume hood and left for 3 hours to allow for the liquid to pass into the beaker. The sample was mixed with a plastic spoon to improve filtration rate. The yield after filtration was 1280 g clear yellowish solution of sunflower oil-like viscosity. The said solution was transferred into a 2 L plastic bottle.
5. An aliquot part of the said filtered clear solution with mass 2.0644 g was measured via 5 mL plastic syringe into a pre-weighed 20 mL glass vial (without snap-on cap). The 20 ml vial with the clear solution was then put into a vacuum oven (Heraeus Vacutherm type, Thermo Scientific™) at 40° C. and pressure between 5 and 50 mbar for about 4 hours to ensure substantial evaporation of the water. The dry polymeric residue was weighed to be 0.28 g and was used to calculate therefore the solid content of the filtered PAA solution to be 13.6% w. This value was multiplied to the overall solution gathered of 1280 g after filtration to obtain to overall amount of 175.36 g of soluble dry PAA polymer obtained as product of degradation of SAP. Dividing the latter value to the starting 300 g of SAP the yield of the degradation reaction was calculated to be about 58.4% w.

The yield represents therefore the ratio of the extracted soluble polymer as product of SAP degradation solution, to the amount of the initial dry pre-existing SAP material. Given that the pre-existing SAP material was a cross-linked network of polyacrylic acid, the extracted soluble polymer was substantially soluble polyacrylic acid.

Preparation of PAA A3-containing Base Polymer BP A3 of Example A3

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 811.0 g of solution comprising aqueous polyacrylic acid PAA A3 obtained as described above of about 6.67% w concentration wherein the weight average molecular weight Mw as determined by Gel Permeation Chromatography was 517,500 Da (test method as described herein above). The 6.67% w aqueous solution of PAA A3 was prepared as a stock solution by diluting and stirring overnight of PAA A3 solution of 13.6% w concentration with the appropriate amount of DI water. A magnetic stirrer, capable of mixing the whole content (when liquid), was added to the resin kettle and stirring was started.

The full amount of 405.9 g of glacial AA (=acrylic acid) was added to the PAA solution in the resin kettle while stirring was continued.

About 20.0 g of deionized water was taken to dissolve 0.455 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.011 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 2.95 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 497.7 g was added to the resin kettle and stirring was continued as a homogeneous solution was obtained within 1-5 minutes.

A thermometer was introduced and in total 281.8 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about minimum 10 min or up to 1 hour of Argon purging and stirring, about 0.025 g (about 1-2 droplets) of 1% aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 4 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~350 g | >710 μm |

The fractions "fines" and "crude" have been discarded and not used further.

Procedure to Obtain the PAA Used in Example A4 (=PAA A4) From Degradation of Pre-Existing SAP Material: Ultraviolet Light Mediated Degradation of Pre-Existing SAP Material The pre-existing SAP material (in the form of pre-existing SAP particles) used for degradation is commercially available in Pampers Baby Dry as marketed in Germany in 2020.

The pre-existing SAP material was mixed with RO (reverse osmosis) water in a Quadro mixer to produce a feed stream (in the form of a gel) with 2.5 wt % SAP and 97.5 wt % RO water. Starting viscosity of the gel was around 840 Pa·s. About 140 mL of the feed stream was loaded in a syringe and fed into a Fusion UV Curing system (FUSION UV SYSTEMS, Inc., Maryland, USA; Hg lamp (H-Bulb) with 300 W/in. and 2.74 W/cm2 power measured by the UV PowerMAP® #20082105 A/B/C/V (EIT, Inc.; Sterling, VA)) in a 6 mm external diameter (OD) (3.68 mm internal diameter (ID)) quartz tube and at a rate of 6 mL/min using a syringe pump (New Era Pump Systems, Inc., Farmingdale, N.Y.; model NE-1000 single syringe pump). The UV lamp was set perpendicular to the quartz tube, the length of the quartz tube exposed to the UV irradiation was estimated to be 15 cm, the longitudinal axis of the quartz tube was about 8 mm above the focal point of the UV lamp, and the residence time of the feed stream in the irradiation zone was 16 s and UV irradiation energy calculated as 1.4 MJ/kg SAP. The viscosity of the product stream was measured with a cup and bob fixture in steady mode, and at 4 s-1 it was measured as 155 mPa·s Preparation of PAA A4-Containing Base Polymer BP A4 of Example A4

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 1043.1 g of solution comprising aqueous PAA-A4 obtained as described above, of about 2.68% w concentration wherein the weight average molecular weight Mw as determined by Gel Permeation Chromatography was 1,080 kDa (test method as described herein above). A magnetic stirrer, capable of mixing the whole content (when liquid), was added to the resin kettle and stirring was started.

The full amount of 432.1 g of glacial AA (=acrylic acid) was added to the PAA solution in the resin kettle while stirring was continued.

About 20.0 g of deionized water was taken to dissolve 0.483 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.011 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 3.22 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 174.0 g was added to the resin kettle and stirring was continued as a homogeneous solution was obtained within 1-5 minutes. A thermometer was introduced and in total 347.2 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, about 0.020 g (about 1-2 droplets) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 4 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 μm | 150-710 μm ~350 g | >710 μm |

The fractions "fines" and "crude" have been discarded and not used further.

Procedure to Obtain the PAA Used in Example A5 (=PAA A5) from Degradation of Pre-Existing SAP Material: Liquid Whistle (LW) Mediated Mechanical Energy Degradation)

The pre-existing SAP material (in the form of pre-existing SAP particles) used for degradation is commercially available in Pampers Baby Dry as marketed in Germany in 2020.

The pre-existing SAP material was mixed with RO (=reverse osmosis) water in an agitation tank system similar to EnSight Solutions Likwifier LORSS series, equipped with approximately 20 gallon working capacity tank, top mounted scrap surface agitator, bottom 6 hole/3 wing rotor-stator high shear impeller to produce a feed stream (in the form of a gel) with 2.5 wt % SAP and 97.5 wt % RO water. The gel had a viscosity of 841 Pa·s. The feed stream was fed into the Liquid Whistle apparatus (LW; Model-A Sonolator; Sonic Corp., Stratford, CT); ellipsoidal orifice dimensions: width was 2×0.0375 in.=1.9 mm, height was 2×0.012 in.=0.6 mm (hydraulic diameter was calculated as 1.7 mm), land length was 1 mm, and volume $V=\pi \times$(width)×(height)×(land length)/4=0.9 mm$^3$) (the ellipsoidal orifice had a cross-sectional surface area of about 1.3 mm$^2$) with flowrate of about 8 L/min and pressure of about 4,500 psi (310 bar), and the product stream was recirculated back into the agitation tank system. The tank volume was passed through the LW apparatus about 8 times, representing a total residence time of about 40 ms in the LW chamber region (about 5 ms per pass). The energy density achieved from the mixing device was about 62 MJ/m$^3$ (about 2.48 MJ/kg SAP).

The actual final solid content of the product was determined to be 2.73% wt via placing 3.00 g thereof in a pre-weighed glass vial of 40 mL volume and placing said vial without cap inside a vacuum oven.

Preparation of PAA A5-containing Base Polymer BP A5 of Example A5

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 1024.0 g of solution comprising aqueous PAA A5 obtained as described above, of about 2.73% w concentration wherein the weight average molecular weight Mw as determined by Gel Permeation Chromatography was 418 kDa (test method as described herein above). A magnetic stirrer, capable of mixing the whole content (when liquid), was added to the resin kettle and stirring was started.

The full amount of 432.1 g of glacial AA (=acrylic acid) was added to the PAA solution in the resin kettle while stirring was continued.

About 20.0 g of deionized water was taken to dissolve 0.484 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.012 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 3.14 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 193.0 g was added to the resin kettle and stirring was continued as a homogeneous solution was obtained within 1-5 minutes.

A thermometer was introduced and in total 347.4 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 1 hour of Argon purging and stirring, about 0.025 g (about 1-2 droplets) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 80° C. within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 µm | 150-710 µm ~350 g | >710 µm |

The fractions "fines" and "crude" have been discarded and not used further.

Preparation of Base Polymer BP A6 of Example A6

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 447.0 g of solution comprising aqueous polyacrylic acid (PAA) of about 2.5% w concentration wherein the weight average molecular weight Mw as reported by the supplier Sigma-Aldrich is 1,000 kDa. The 2.5% w aqueous solution was prepared earlier as a stock solution by mixing in and stirring overnight of 50.0 g of dry PAA polymer with reported Mw of about 1,000 kDa (Sigma Aldrich) into 1950.0 g of DI water in a 3 L glass beaker. A magnetic stirrer, capable of mixing the whole content (when liquid), was added and stirring was started.

The full amount of 218.3 g of glacial AA (=acrylic acid) was added to the PAA solution in the resin kettle while stirring was continued.

About 20.0 g of deionized water was taken to dissolve 0.246 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.055 g of "ASC" (=Ascorbic Acid, from Sigma Aldrich) e.g. in a glass vial of 40 mL volume. The vessel with the "ASC" solution was closed with a plastic snap-on cap and set aside.

About 30 g of deionized water was taken to dissolve 1.59 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 159.9 g was added to the resin kettle and stirring was continued as a homogeneous solution was obtained within 1-5 minutes.

A thermometer was introduced and in total 173.2 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 30 min of Argon purging and stirring, about 1.015 g of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 15 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° C. within 60 minutes. Once the temperature starts to drop from a maximal value, the resin kettle was transferred into a circulation oven (e.g. Binder FED 720 from Binder GmbH) and kept at about 60° C. for about 20 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours. The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
|---|---|---|---|
| sieved fraction yield | <150 µm | 150-710 µm ~200 g | >710 µm |

The fractions "fines" and "crude" have been discarded and not used further.

Preparation of Base Polymer BP A7 of Example A7

A 2,000 ml resin kettle (equipped with a four-necked glass cover closed with septa, suited for the introduction of a thermometer, syringe needles) was placed into an ice bath filled with about 1 liter of water, 100 g of sodium chloride and about 200 g of ice such that the mixture covers about half the height of the resin kettle. The resin kettle was charged with about 1240.8 g of solution comprising aqueous polyacrylic acid (PAA) of about 9.0% w concentration wherein the viscosity average molecular weight Mv reported by the supplier Sigma Aldrich was reported to be 450,000 Da. The 9.0% w aqueous solution was prepared earlier as a stock solution by mixing in and stirring overnight of 135 g of dry PAA polymer with reported Mv 450,000 Da (Sigma Aldrich) into 1365.0 g of DI water in a 3 L glass beaker. A magnetic stirrer, capable of mixing the whole content (when liquid), was added and stirring was started.

The full amount of 348.3 g of glacial AA (=acrylic acid) was added to the PAA solution in the resin kettle while stirring was continued.

About 20.0 g of deionized water was taken to dissolve 0.393 g of "KPS" (=potassium peroxydisulfate, from Sigma Aldrich) e.g. in a glass vial of 40 mL volume. The vessel with the "KPS" solution was closed with a plastic snap-on cap and set aside.

About 10.0 g of deionized water was taken to dissolve 0.009 g of "ASC" (=Ascorbic Acid, from Sigma Aldrich) e.g. in a glass vial of 40 mL volume. The vessel with the "ASC" solution was closed with a plastic snap-on cap and set aside.

About 25 g of deionized water was taken to dissolve 2.54 g of "PEG700-DA" (=polyethylene glycol diacrylate of Mn~700 Da from Sigma Aldrich) e.g. in a 50 mL glass beaker. The beaker with the "PEG700-DA" solution was covered e.g. with parafilm and set aside.

The remaining amount of water up to a final weight of 60.3 g was added to the resin kettle and stirring was continued as a homogeneous solution was obtained within 5 minutes.

A thermometer was introduced and in total 347.3 g of 50% w NaOH (sodium hydroxide) solution (for analysis, from Merck KGaA) were added subsequently in portions such that the temperature was below 30° C.

The "PEG700-DA" solution was added to the mixture of PAA, AA and NaOH solution at a temperature below 30° C. while stirring was continued.

Then, the resin kettle was closed, the ice bath underneath removed, and a pressure relief was provided e.g. by puncturing two syringe needles through the septa. The solution was then purged vigorously with argon via an 80 cm injection needle at about 0.4 bar while stirring at about 400 rpm. The argon stream was placed close to the stirrer for efficient and fast removal of dissolved oxygen.

After about 30 min of Argon purging and stirring, about 0.2 g (about 10 droplets) of 1% w aqueous solution of hydrogen peroxide $H_2O_2$ (Sigma-Aldrich) was added via 1 mL plastic pipette to the "KPS" solution, and the latter was then added to the reaction mixture via plastic funnel inserted temporarily in one of the resin kettle cover necks while stirring and Argon purging was continued. Thereafter the "ASC" solution was added to the reaction mixture at a temperature of about 20° C. via plastic funnel inserted temporarily in one of the resin kettle cover necks while stirring and Argon purging was continued.

After the initiator solutions "KPS" and "ASC" were mixed with the reaction mixture, stirring and Argon purging was continued but the Argon needle was pulled a few cm above the liquid. Typically, within 3 min of "ASC" solution addition, the solution characteristically starts to become turbid or a sudden increase in viscosity was observed, typically at temperatures about room temperature. A "gel point" was observed and recorded when the stirbar was not able to rotate freely at the bottom of the resin kettle and the stirring was therefore stopped. Purging with argon was continued at a reduced flow rate (0.2 bar).

The temperature was monitored; typically, it rises from about 20° C. to about 70° within 60 minutes. Once the temperature starts to drop from a maximal value, the resin kettle was transferred into a circulation oven (e.g. Binder FED 720 from Binder GmbH) and kept at about 60° C. for about 18 hours.

After this time, the oven was switched off and the resin kettle was allowed to cool down for about 2 hours while remaining in the oven. After that, the gel was removed and broken manually or cut with scissors into smaller pieces. The gel was grinded with a grinder (X70G from Scharfen Slicing Machines GmbH with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720 from Binder GmbH) at about 120° C. for about 20 hours.

The residual moisture content of the dried gel was about 3% by weight (see UPM test method for description of how to determine moisture content).

The dried gel was then ground using a centrifuge mill (Retsch ZM 200 from Retsch GmbH with vibratory feeder DR 100 (setting 50-60), interchangeable sieve with 1.5 mm opening settings, rotary speed 8000 rpm). The milled polymer was then sieved via a sieving machine (AS 400 control from Retsch with sieves DIN/ISO 3310-1 at about 250 rpm for about for 5-10 min) to the following particle size cuts with the following yields:

|  | fines | Collected fraction | crude |
| --- | --- | --- | --- |
| sieved fraction yield | <150 μm | 150-710 μm ~350 g | >710 μm |

The fractions "fines" and "crude" have been discarded and not used further.

Surface Crosslinking Treatment (Hereinafter Referred to as "SXL") of Base Polymer Particles BP A1 to BP A7 and BP C1 to BP C8 in Order to Obtain Examples A1 to A7 and Comparative Examples C1 to C8

Equipment List:
  Glassware, one way pipette, spatula, spoon to prepare solution and weigh in absorbent materials
  Glass Beaker: 250 ml opening ø 70 mm
  Balance: Sartorius or equivalent; accuracy 0.01 g
  Analytical balance: Mettler or equivalent; accuracy 0.0001 g
  Electrical stand stirrer: IKA Eurostar power control visc (Range 50-2000 rpm) or equivalent
  With Stirrer: PTFE Propeller stirrer 4-bladed_ø 50 mm
  Pipette: Eppendorf Multi stream or equivalent
  Aluminum foil for covering
  Circulation oven: Binder FD 240 or equivalent
  Equipment to determine Moisture: Halogen Moisture Balance Mettler or equivalent
  Sieve machine: Retch AS 200 control "g" or equivalent
  With Sieves: stainless steel: DIN/ISO 3310-1 ø10 mm Preparation of Solutions:
  Aluminum lactate solution
  Prepare 1 kg 15 w % Aluminum lactate solution in deionized water (MilliporeQ of conductivity <1.6 μS/cm) by adding 850 g of deionized water to 150 g of Aluminum lactate.
  Surface crosslinking solutions (SXL solutions) (see table A):
  The used Denacol concentrations were prepared according to Table 3, each in snap cap jars of volume about 50 ml.

To prepare the solutions, the Denacol bottle or container (ca. 1 L) was taken out of the fridge and let to stay out to thermally equilibrate for ca. 30 min before preparing the solutions.

Solutions were prepared as follows:

Different respective concentrations, for the given examples, of Denacol EX-810, DN-810 ex Nagase Co. Ltd.) were prepared by adding the amount shown in Table 3 to the snap cap plastic jar which was then filled to 20 g with 1,2-Propanediol (Merck KGaA).

TABLE 3

| Surface crosslinking agent | Examples/ comparative examples | Concentration (in wt. %) | Preparation of solution |
|---|---|---|---|
| Denacol EX-810 | A1-A5, C1-C4 | 8% | 1.6 g DN-810 filled in with 1,2 Propanediol to 20 g |
| Denacol EX-810 | C5 | 10% | 2.0 g DN-810 filled in with 1,2 Propanediol to 20 g |
| Denacol EX-810 | A6-A7, C6-C8 | 7% | 1.4 g DN-810 filled in with 1,2 Propanediol to 20 g |

Execution of SXL Procedure:

Each of the respective dry base polymer particles BP A1 to BP A7 and BP C1 to BP C8 was weighed to be 20-30 g and recorded to ±0.1 g and placed in a separate 250 ml glass beaker so that the filling height is ≤25% of the overall height. Exact amounts are given in Table 5.

The base polymer particles were mixed at 600+/−50 rpm with a PTFE stirrer into the beaker. The stirrer was just touching the bottom of the beaker. The base polymer particles needed to be stirred until good fluidization of the bed is achieved.

The requested amounts of solutions were added with an Eppendorf pipette, step by step like described below and the actual quantities are given in Table B. (Speed setting of Eppendorf pipette: Middle speed)

Step 1:

The amount of Aluminum Lactate Solution was added into the center of stirring agitation. Afterwards, the stirring speed was raised to 2000+/−50 rpm. Stirred for approximately 15 seconds and continued with Step 2. If necessary, covered beaker with e.g. aluminum foil to avoid jumping out of material.

Step 2:

The amount of SXL solution was added into the center of stirring agitation. Stirred for approximately 15 seconds and continued with Step 3.

Step 3:

Amount of deionized water (3 wt % based on sample weight) was added into the center of stirring agitation. Stirred for approximately 15 seconds. After stopping stirrer transferred the material into a heat resistant wide-mouth glass vial (e.g. crystallizing dish) and distributed it evenly. Took loose material only and left strong stacked material on wall in beaker. Removed loose material by slight tapping outside on wall of beaker or by use of spatula. Avoided scratching out. Covered the wide mouth glass vial with aluminum foil and stored it into a fume hood at room temperature for approximately 16 h to 18 h (overnight is recommended) and afterwards heated the material in the oven at requested temperature and time (e.g. Surface crosslinking Denacol heat up period of 20 min from room temperature to 120° C. in addition to the 3 h heating time).

After 2 h 20 min heating time, the aluminum foil was half-way open and stayed like this for the remaining 1 h of heating to drive moisture lower than 1% w.

After heating time, removed container from the oven and placed the material into a fume hood to cool down to room temperature, for approximately 15 min.

The final polymers were tested for moisture, the results are shown in Table 4.

TABLE 4

| Example | Moisture, wt % |
|---|---|
| A1 | 0.5 |
| A2 | 0.4 |
| A3 | 0.4 |
| A4 | 0.4 |
| A5 | 0.5 |
| A6 | 0.6 |
| A7 | 0.7 |
| C1 | 0.4 |
| C2 | 0.5 |
| C3 | 0.8 |
| C4 | 0.4 |
| C5 | 0.5 |
| C6 | 0.5 |
| C7 | 0.3 |
| C8 | 0.5 |

TABLE 5

| Examples and comparative examples | Amount of Base Polymer Particles treated (in g) | Denacol Ex810 concentration, (in wt %) | Overall Denacol Ex810 add-on vs. polymer (in wt %) | Overall Aluminium lactate add-on vs polymer, (in wt %) | Added deionized water (in wt % vs polymer) |
|---|---|---|---|---|---|
| A1-A5, C1-C2, C4 | 30.0 | 8% | 0.080 | 0.5 | 12.5 |
| C3 | 20.0 | 8% | 0.144 | 0.9 | 12.5 |
| C5 | 30.0 | 10% | 0.100 | 0.9 | 12.5 |
| A6-A7, C6-C8 | 30.0 | 7% | 0.070 | 0.5 | 12.5 |

The quantities of Denacol Ex810 were selected such that the resulting examples and comparative examples exhibited CRC above 25 g/g and EFFC between 23 and 29 g/g (see Table 6)

TABLE 6

Performance of Examples A1 to A7 and Comparative Examples C1 to C8

| EXAMPLE | CRC[1], g/g | Extractables[1], % w | Ratio Extract[1] [% w] to CRC[1] [g/g] | CRC[2], g/g | EFFC[2], g/g | UPM[2], g/g |
|---|---|---|---|---|---|---|
| A1 | 46.8 | 10.1 | 0.22 | 30.7 | 27.8 | 32 |
| A2 | 44.3 | 8.3 | 0.19 | 30.6 | 27.6 | 33 |
| A3 | 37.6 | 7.9 | 0.21 | 27 | 25 | 87 |
| A4 | 42.9 | 9.7 | 0.23 | 30.9 | 27.4 | 27 |
| A5 | 44.1 | 9.9 | 0.22 | 30.2 | 27.1 | 36 |
| A6 | 44.2 | 8.4 | 0.19 | 30.0 | 27.4 | 46 |
| A7 | 52.7 | 16.6 | 0.31 | 31.8 | 27.5 | 21 |
| C1 | 46.3 | 11.1 | 0.24 | 32 | 27.5 | 15 |
| C2 | 46.3 | 11.1 | 0.24 | 29.9 | 26.5 | 31 |
| C3 | 35.3 | 7.4 | 0.21 | 26.3 | 23.9 | 54 |
| C4 | 52.6 | 23.1 | 0.44 | 31.8 | 26.5 | 18 |
| C5 | 47.1 | 22 | 0.47 | 29.5 | 25.1 | 38 |
| C6 | 51.6 | 24.6 | 0.48 | 33.4 | 25.9 | 7 |
| C7 | 45.8 | 13.6 | 0.30 | 30.7 | 26.9 | 33 |
| C8 | 44.8 | 13.9 | 0.31 | 30.6 | 26.6 | 35 |

[1]Value for base polymer particle
[2]Value for SAP particle after surface cross-linking Examples A1 to A7 all have a ratio of average diameter of gyration $2*R_g$ to average distance $R_{xl}$ between neighboring crosslinks of well above 1.1. Comparative examples C4 to C8 have a ratio of average diameter of gyration $2*R_g$ to average distance $R_{xl}$ between neighboring crosslinks of well below 1.0 (comparative examples C1 to C3 do not comprise any s-PAA polymers and hence, the ratio does not apply). As is reflected by the results, SAP particles having a ratio of above 1.1 have improved performance properties, especially improved ratio of extractables to capacity (CRC) vs. comparative examples when comparing examples and comparative examples with similar amounts of s-PAA polymers (i.e. similar percent of s-PAA polymers based on total weight of the SAP particles).

As can be seen from the results, the ratio of extractables to capacity (CRC) of examples A1 to A6 is as good as or even better than the results for comparative examples C1 to C3, which have no s-PAA polymers added.

Example A7 exhibits good performance properties despite comprising relatively high amounts of s-PAA polymers (20 weight-%). Amount of extractables is 16.6% for the base polymer, i.e. before surface cross-linking. Amount of extractables typically decreases after surface cross-linking (due to higher density of cross-links between polymer chains on the particle surface), so amount of extractables will be even below 16.6% for example A7 after surface cross-linking.

Comparative examples C4 to C6 exhibit high ratio of extractables to capacity (CRC). Comparative examples C7 and C8 have a ratio similar to the ratio to example A7. However, example A7 has an amount of s-PAA polymers of 20 weight-% whereas comparative examples C7 and C8 only have an amount of s-PAA polymers of 5 weight-%.

Comparative examples C5 and C6 only differ from comparative examples C7 and C8 by the amount of s-PAA polymers. The results show that increase the amount of s-PAA polymers from 5 weight-% (C7 and C8) to 10 weight-% (C5 and C6) has a significant adverse impact on the ratio of extractables to capacity (CRC). Compared thereto, using s-PAA polymers with relatively high weight average molecular weight in examples A1 to A7 considerably improves the ratio of extractables to capacity (CRC), i.e. the amount of extractables is considerably lower relative to the capacity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A superabsorbent polymer material comprising cross-linked polyacrylic acid and salts thereof, the superabsorbent polymer material further comprising at least 3.0 weight-%, based on the total weight of the superabsorbent polymer material, of soluble polyacrylic acid polymers,
wherein the cross-linked polyacrylic acid and salts thereof have an average distance $R_{xl}$ between neighboring cross-links, as calculated for the superabsorbent polymer material loaded with 20 g of saline with 0.9%w NaCl per gram of dry superabsorbent polymer material, and
wherein the at least 3.0 weight-% of soluble polyacrylic acid polymers have an average diameter of gyration $2*R_g$, and
wherein the ratio of $2*R_g$ to $R_{xl}$ is at least 1.1.

2. The superabsorbent polymer material of claim 1, wherein the soluble polyacrylic acid polymers have a weight average molecular weight $M_w$ of from about 250 kDa to about 3 MDa.

3. The superabsorbent polymer material of claim 1, wherein the average distance between neighboring cross-links in the polymer network $R_{xl}$ is at least about 15 nm, and not more than about 50 nm.

4. The superabsorbent polymer material of claim 1, wherein the diameter of gyration $2*R_g$ of the soluble polyacrylic polymers is at least about 20 nm, and not more than about 100 nm.

5. The superabsorbent polymer material of claim 1, wherein the soluble polyacrylic acid polymers are comprised by the superabsorbent polymer material in an amount up to 50.0 weight-%, based on the total weight of the superabsorbent polymer material.

6. The superabsorbent polymer material of claim 1, wherein the superabsorbent polymer material is in the form of superabsorbent polymer particles.

7. The superabsorbent polymer material of claim 6, wherein the superabsorbent polymer particles are surface cross-linked.

8. The superabsorbent polymer material of claim 1, wherein the superabsorbent polymer material has an amount of extractables of less than 15.0 weight-%.

9. The superabsorbent polymer material of claim 1, wherein the superabsorbent polymer material has a capacity measured as Centrifuge Retention Capacity (CRC) in accordance the test method set out herein of at least 20 g/g.

10. The superabsorbent polymer material of claim 1, wherein the soluble polyacrylic acid polymers are obtained from pre-existing recycled post-consumer superabsorbent polymer material and/or obtained from pre-existing recycled post-industrial superabsorbent polymer material.

11. An absorbent article comprising the superabsorbent polymer material of claim 1.

* * * * *